(12) United States Patent
Kliger et al.

(10) Patent No.: US 8,612,016 B2
(45) Date of Patent: Dec. 17, 2013

(54) MONITORING, ANALYSIS, AND REGULATION OF EATING HABITS

(75) Inventors: Anat Kliger, Herzliya (IL); Shai Policker, Tenafly, NJ (US); Ricardo Aviv, Vienna (AT)

(73) Assignee: Metacure Limited, Hamiton (BM)

( * ) Notice: Subject to any disclaimer, the term of this patent is extended or adjusted under 35 U.S.C. 154(b) by 485 days.

(21) Appl. No.: 11/573,722

(22) PCT Filed: Aug. 18, 2005

(86) PCT No.: PCT/IL2005/000904
§ 371 (c)(1),
(2), (4) Date: Dec. 18, 2008

(87) PCT Pub. No.: WO2006/018851
PCT Pub. Date: Feb. 23, 2006

(65) Prior Publication Data
US 2009/0118797 A1    May 7, 2009

Related U.S. Application Data

(60) Provisional application No. 60/602,550, filed on Aug. 18, 2004.

(51) Int. Cl.
*A61B 5/04* (2006.01)
*A61B 5/103* (2006.01)
*A61B 5/117* (2006.01)
*A61N 1/00* (2006.01)

(52) U.S. Cl.
USPC ............... 607/62; 607/40; 607/41; 607/133; 600/546; 600/593

(58) Field of Classification Search
USPC ................. 607/40, 41, 62, 133; 600/546, 593
See application file for complete search history.

(56) References Cited

U.S. PATENT DOCUMENTS

| | | | |
|---|---|---|---|
| 3,411,507 A | 11/1968 | Wingrove | |
| 3,516,412 A | 6/1970 | Ackerman | |

(Continued)

FOREIGN PATENT DOCUMENTS

| | | |
|---|---|---|
| EP | 0057048 | 8/1982 |
| EP | 0057048 | 8/1982 |

(Continued)

OTHER PUBLICATIONS

OA issued Oct. 24, 2008 in Applicant's European Patent Appln. No. EP 02 724 592.7.

(Continued)

*Primary Examiner* — Michael Kahelin
*Assistant Examiner* — Lindsey G Hankins
(74) *Attorney, Agent, or Firm* — William H. Dippert; Eckert Seamans Cherin & Mellott, LLC

(57) ABSTRACT

Gastric apparatus is provided, including one or more sensors, adapted to generate respective sensor signals responsive to activity of a gastrointestinal tract of a subject. A control unit is configured with an eating detection threshold selected from the group consisting of: a predetermined threshold, and a threshold determined during a calibration procedure. The control unit is adapted to receive and analyze the sensor signals, and identify an aspect of at least one of the sensor signals indicative of periodic activity of the gastrointestinal tract. The control unit modifies the eating detection threshold responsive to identifying the aspect of the signals that is indicative of the periodic activity, and determines that an eating event has occurred responsive to the modified eating detection threshold and at least one of the analyzed sensor signals. Other embodiments are also described.

25 Claims, 11 Drawing Sheets

(56) References Cited

U.S. PATENT DOCUMENTS

| | | |
|---|---|---|
| 3,737,579 A | 6/1973 | Bolduc |
| 4,000,745 A | 1/1977 | Goldberg et al. |
| 4,010,758 A | 3/1977 | Rockland et al. |
| 4,133,315 A | 1/1979 | Berman et al. |
| 4,177,818 A | 12/1979 | De Pedro |
| 4,235,246 A | 11/1980 | Weiss |
| 4,280,503 A | 7/1981 | Ackerman |
| 4,313,448 A | 2/1982 | Stokes |
| 4,357,946 A | 11/1982 | Dutcher et al. |
| 4,378,023 A | 3/1983 | Trabucco |
| 4,416,267 A | 11/1983 | Garren et al. |
| 4,452,254 A | 6/1984 | Goldberg et al. |
| 4,485,805 A | 12/1984 | Foster, Jr. |
| 4,592,339 A | 6/1986 | Kuzmak et al. |
| 4,823,808 A | 4/1989 | Clegg et al. |
| 4,975,682 A | 12/1990 | Kerr et al. |
| 5,074,868 A | 12/1991 | Kuzmak |
| 5,101,814 A | 4/1992 | Palti |
| 5,103,804 A | 4/1992 | Abele et al. |
| 5,105,812 A | 4/1992 | Corman |
| 5,188,104 A | 2/1993 | Wernicke et al. |
| 5,190,041 A | 3/1993 | Palti |
| 5,226,429 A | 7/1993 | Kuzmak |
| 5,234,454 A | 8/1993 | Bangs |
| 5,247,938 A | 9/1993 | Silverstein et al. |
| 5,263,480 A | 11/1993 | Wernicke et al. |
| 5,292,344 A | 3/1994 | Douglas |
| 5,314,463 A | 5/1994 | Camps et al. |
| 5,368,028 A | 11/1994 | Palti |
| 5,423,872 A | 6/1995 | Cigaina |
| 5,449,368 A | 9/1995 | Kuzmak |
| 5,514,175 A | 5/1996 | Kim et al. |
| 5,540,730 A | 7/1996 | Terry et al. |
| 5,551,425 A | 9/1996 | Essen-Moller |
| 5,601,604 A | 2/1997 | Vincent |
| 5,690,691 A | 11/1997 | Chen et al. |
| 5,704,368 A | 1/1998 | Asano et al. |
| 5,716,385 A | 2/1998 | Mittal et al. |
| 5,741,211 A | 4/1998 | Renirie et al. |
| 5,792,210 A | 8/1998 | Wamubu et al. |
| 5,795,304 A | 8/1998 | Sun et al. |
| 5,836,994 A | 11/1998 | Bourgeois |
| 5,837,006 A | 11/1998 | Ocel et al. |
| 5,861,014 A | 1/1999 | Familoni |
| 5,868,141 A | 2/1999 | Ellias |
| 5,891,185 A | 4/1999 | Freed et al. |
| 5,919,216 A | 7/1999 | Houben et al. |
| 5,938,669 A | 8/1999 | Klaiber et al. |
| 5,979,449 A | 11/1999 | Steer |
| 5,991,649 A | 11/1999 | Garfield et al. |
| 5,995,872 A | 11/1999 | Bourgeois |
| 6,026,326 A | 2/2000 | Bardy |
| 6,041,258 A | 3/2000 | Cigaina et al. |
| 6,067,991 A | 5/2000 | Forsell |
| 6,083,249 A | 7/2000 | Familoni |
| 6,091,992 A | 7/2000 | Bourgeois |
| 6,092,528 A | 7/2000 | Edwards |
| 6,093,167 A | 7/2000 | Houben et al. |
| 6,104,955 A | 8/2000 | Bourgeois |
| 6,115,635 A | 9/2000 | Bourgeois |
| 6,129,685 A | 10/2000 | Howard |
| 6,132,372 A | 10/2000 | Essen-Moller |
| 6,135,978 A | 10/2000 | Houben |
| 6,216,045 B1 | 4/2001 | Black et al. |
| 6,243,607 B1 | 6/2001 | Mintchev |
| 6,249,697 B1 | 6/2001 | Asano et al. |
| 6,261,280 B1 | 7/2001 | Houben et al. |
| 6,334,073 B1 | 12/2001 | Levine |
| 6,363,937 B1 | 4/2002 | Hovda et al. |
| 6,381,495 B1 | 4/2002 | Jenkins |
| 6,405,732 B1 | 6/2002 | Edwards et al. |
| 6,411,842 B1 | 6/2002 | Cigaina et al. |
| 6,415,178 B1 | 7/2002 | Ben-Haim et al. |
| 6,427,089 B1 | 7/2002 | Knowlton |
| 6,449,511 B1 | 9/2002 | Mintchev |
| 6,454,699 B1 | 9/2002 | Forsell |
| 6,535,764 B2 | 3/2003 | Imran et al. |
| 6,571,127 B1 | 5/2003 | Ben-Haim et al. |
| 6,572,542 B1 | 6/2003 | Houben et al. |
| 6,584,348 B2 | 6/2003 | Glukhovsky |
| 6,591,137 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,612,983 B1 | 9/2003 | Marchal |
| 6,652,444 B1 | 11/2003 | Ross |
| 6,658,297 B2 | 12/2003 | Loeb |
| 6,684,104 B2 | 1/2004 | Gordon |
| 6,735,477 B2 | 5/2004 | Levine |
| 6,745,079 B2 | 6/2004 | King |
| 6,754,536 B2 | 6/2004 | Swoyer et al. |
| 6,826,428 B1 | 11/2004 | Chen et al. |
| 6,832,114 B1 | 12/2004 | Whitehurst |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,906 B2 | 7/2005 | Long |
| 6,939,349 B2 | 9/2005 | Fleischman et al. |
| 6,947,792 B2 | 9/2005 | Ben-Haim et al. |
| 6,952,613 B2 | 10/2005 | Swoyer et al. |
| 7,006,871 B1 | 2/2006 | Darvish et al. |
| 7,043,295 B2 | 5/2006 | Starkebaum |
| 7,054,690 B2 | 5/2006 | Imran |
| 7,076,305 B2 | 7/2006 | Imran et al. |
| 7,076,306 B2 | 7/2006 | Marchal et al. |
| 2001/0011543 A1 | 8/2001 | Forsell |
| 2002/0026141 A1 | 2/2002 | Houben |
| 2002/0103424 A1 | 8/2002 | Swoyer et al. |
| 2002/0161414 A1* | 10/2002 | Flesler et al. ............... 607/40 |
| 2003/0018367 A1 | 1/2003 | DiLorenzo |
| 2003/0045919 A1 | 3/2003 | Swoyer et al. |
| 2003/0055464 A1 | 3/2003 | Darvish et al. |
| 2003/0055467 A1 | 3/2003 | Ben-Haim et al. |
| 2003/0066536 A1 | 4/2003 | Forsell |
| 2003/0144708 A1* | 7/2003 | Starkebaum ............... 607/40 |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0220678 A1 | 11/2003 | Tronnes et al. |
| 2004/0044376 A1 | 3/2004 | Flesler et al. |
| 2004/0059393 A1* | 3/2004 | Policker et al. ............... 607/40 |
| 2004/0088023 A1 | 5/2004 | Imran et al. |
| 2004/0107004 A1 | 6/2004 | Levine et al. |
| 2004/0147816 A1 | 7/2004 | Policker et al. |
| 2004/0158138 A1 | 8/2004 | Kilcoyne et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0236316 A1 | 11/2004 | Danitz et al. |
| 2004/0249421 A1 | 12/2004 | Harel et al. |
| 2005/0020965 A1 | 1/2005 | Rioux et al. |
| 2005/0021101 A1 | 1/2005 | Chen et al. |
| 2005/0055038 A1 | 3/2005 | Kelleher et al. |
| 2005/0065505 A1 | 3/2005 | Ryan |
| 2005/0075654 A1 | 4/2005 | Kelleher |
| 2005/0090873 A1 | 4/2005 | Imran |
| 2005/0096514 A1 | 5/2005 | Starkebaum |
| 2005/0107829 A1 | 5/2005 | Edwards et al. |
| 2005/0143784 A1 | 6/2005 | Imran |
| 2005/0149142 A1* | 7/2005 | Starkebaum ............... 607/40 |
| 2005/0164925 A1 | 7/2005 | Jakubowski et al. |
| 2005/0183732 A1 | 8/2005 | Edwards |
| 2005/0192615 A1 | 9/2005 | Torre et al. |
| 2005/0203500 A1 | 9/2005 | Saadat et al. |
| 2005/0209653 A1 | 9/2005 | Herbert et al. |
| 2005/0222638 A1 | 10/2005 | Foley et al. |
| 2006/0064037 A1 | 3/2006 | Shalon et al. |
| 2006/0074459 A1 | 4/2006 | Flesler et al. |
| 2006/0085045 A1 | 4/2006 | Harel et al. |
| 2006/0142803 A1 | 6/2006 | Mintchev |
| 2006/0173238 A1 | 8/2006 | Starkebaum |

(56) References Cited

U.S. PATENT DOCUMENTS

| | | |
|---|---|---|
| 2006/0184207 A1 | 8/2006 | Darvish et al. |
| 2006/0247718 A1 | 11/2006 | Starkebaum |
| 2006/0264699 A1 | 11/2006 | Gertner |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0092446 A1 | 4/2007 | Haddad et al. |
| 2007/0156177 A1 | 7/2007 | Harel et al. |
| 2007/0179556 A1 | 8/2007 | Ben Haim et al. |
| 2007/0185540 A1 | 8/2007 | Ben-Haim et al. |
| 2007/0299320 A1 | 12/2007 | Policker et al. |
| 2008/0046062 A1 | 2/2008 | Camps et al. |
| 2008/0058889 A1 | 3/2008 | Ben-Haim et al. |
| 2008/0058891 A1 | 3/2008 | Ben-Haim et al. |
| 2008/0065168 A1 | 3/2008 | Bitton et al. |
| 2008/0178684 A1 | 7/2008 | Spehr |
| 2009/0062893 A1 | 3/2009 | Spehr |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2010/0228105 A1 | 9/2010 | Policker et al. |
| 2010/0305468 A1 | 12/2010 | Policker et al. |
| 2010/0324644 A1 | 12/2010 | Levi et al. |

FOREIGN PATENT DOCUMENTS

| | | |
|---|---|---|
| EP | 0129483 | 12/1984 |
| EP | 0129483 | 12/1984 |
| EP | 144705 | 6/1985 |
| EP | 1036545 | 9/2000 |
| EP | 1 447 052 | 8/2004 |
| JP | 2003/319945 | 11/2003 |
| JP | 2003319945 | 11/2003 |
| WO | WO 94/01172 | 1/1994 |
| WO | WO 97/25098 | 7/1997 |
| WO | WO 97/41921 | 11/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2004/112883 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/018851 | 2/2006 |
| WO | WO 2006/035446 | 4/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/118790 | 11/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

International Search Report for WO2006/018851 A3—Issued Feb. 22, 2008 by USPTO

Supplementary European Search Report dated Oct. 7, 2009 for Appln. No. 05774732.1-2305.

CN—Chinese Appln. No. 2004-80027283.3—Office Action issued by CPO dated Jul. 13, 2009.

Jaremko, et al, "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

ShemerovsKii KA, "Effect of feeding on the activity of duodenal smooth muscle in dogs", Biull Eksp Biol Med. Oct. 1978;86(10):394-7. (Abstract only).

U.S. Appl. No. 10/237,263.

An International Search Report and A Written Opinion, both date Oct. 28, 2008, which issued during the prosecution of Applicant's PCT/IL08/00646.

A Supplementary Partial European Search Report dated Feb. 20, 2009, which issued during the prosecution of Applicant's European Patent Application No. EP 02 72 7012.

(56) References Cited

OTHER PUBLICATIONS

International Search Report and The Written Opinion Dated Sep. 2, 2011 From the International Searching Authority Re. Application No. PCT/IL 11/00116.

An Office Action dated Jun. 18, 2013 which issued during the prosecution of European Patent Application No. 04745004.4.

U.S. Patent Application No. 10/237,263.

* cited by examiner

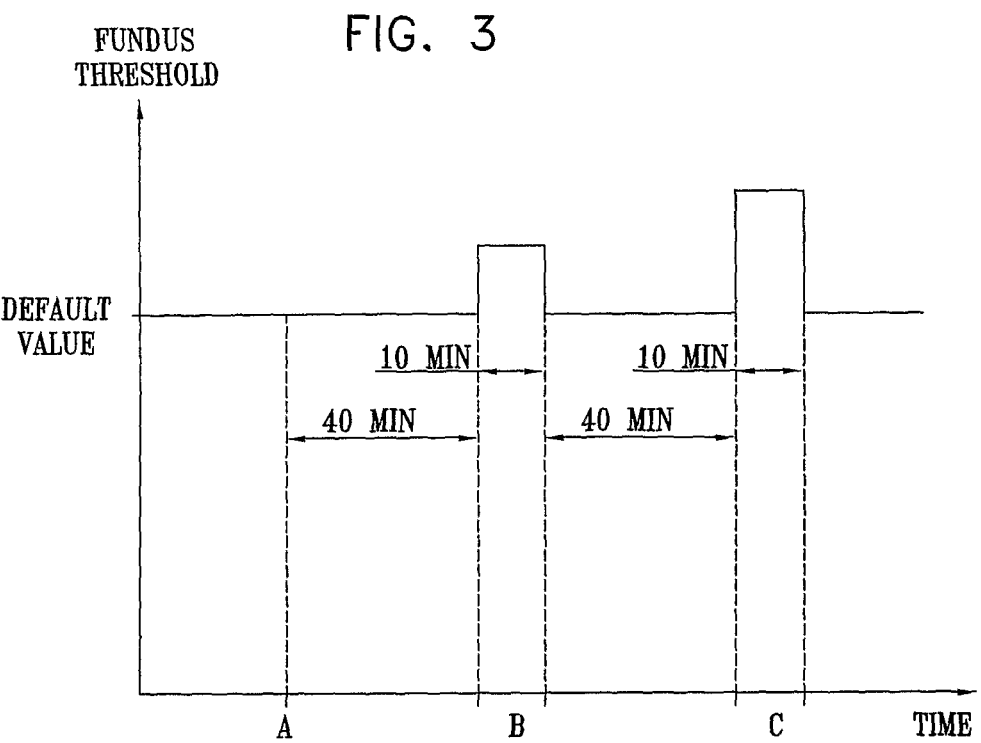
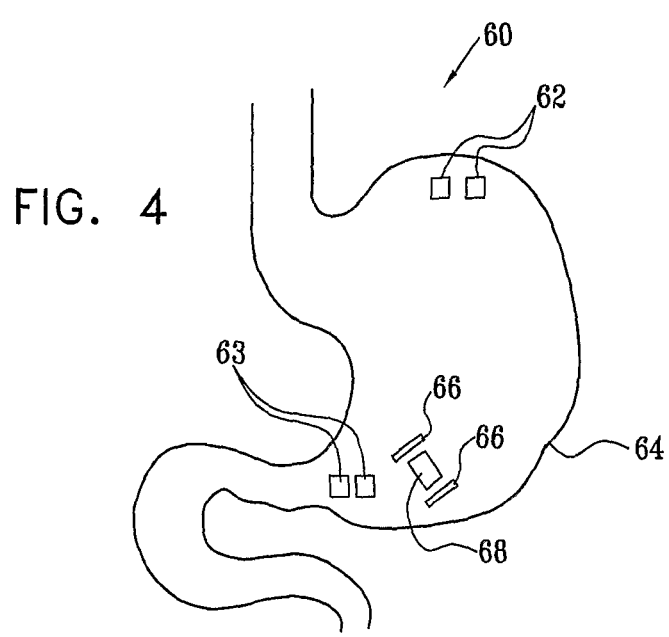

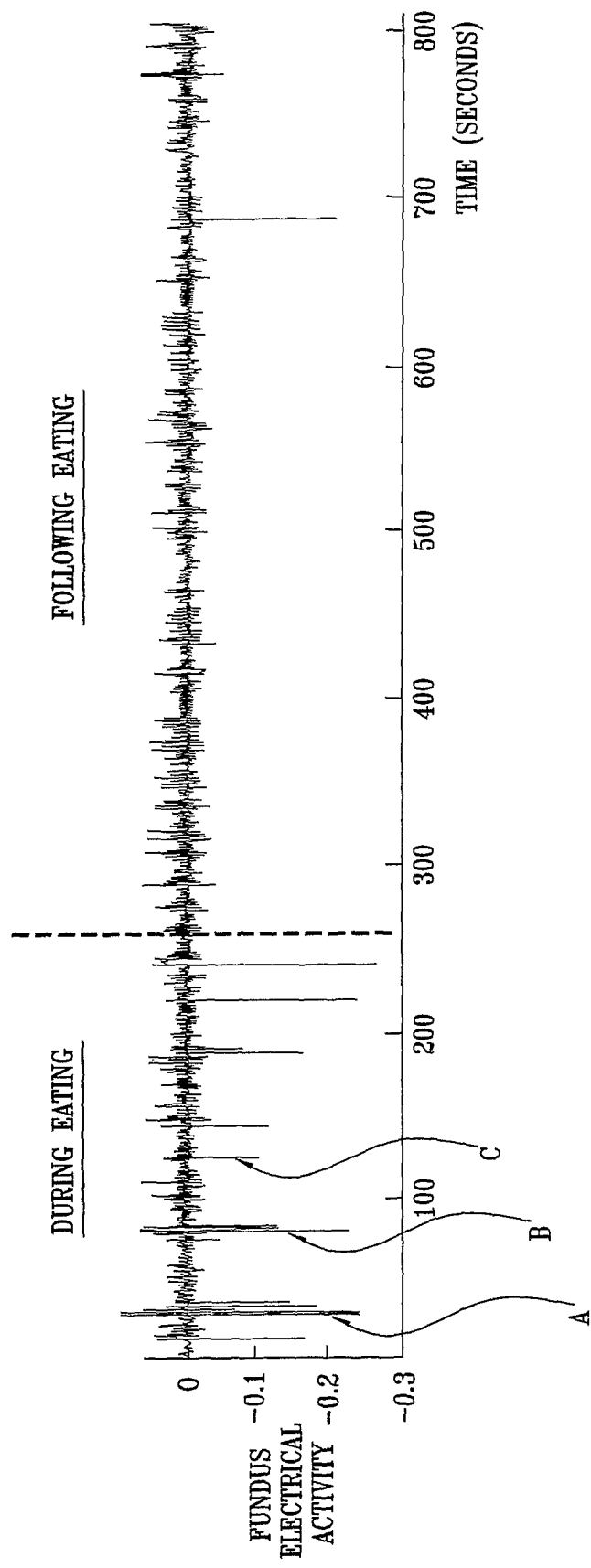

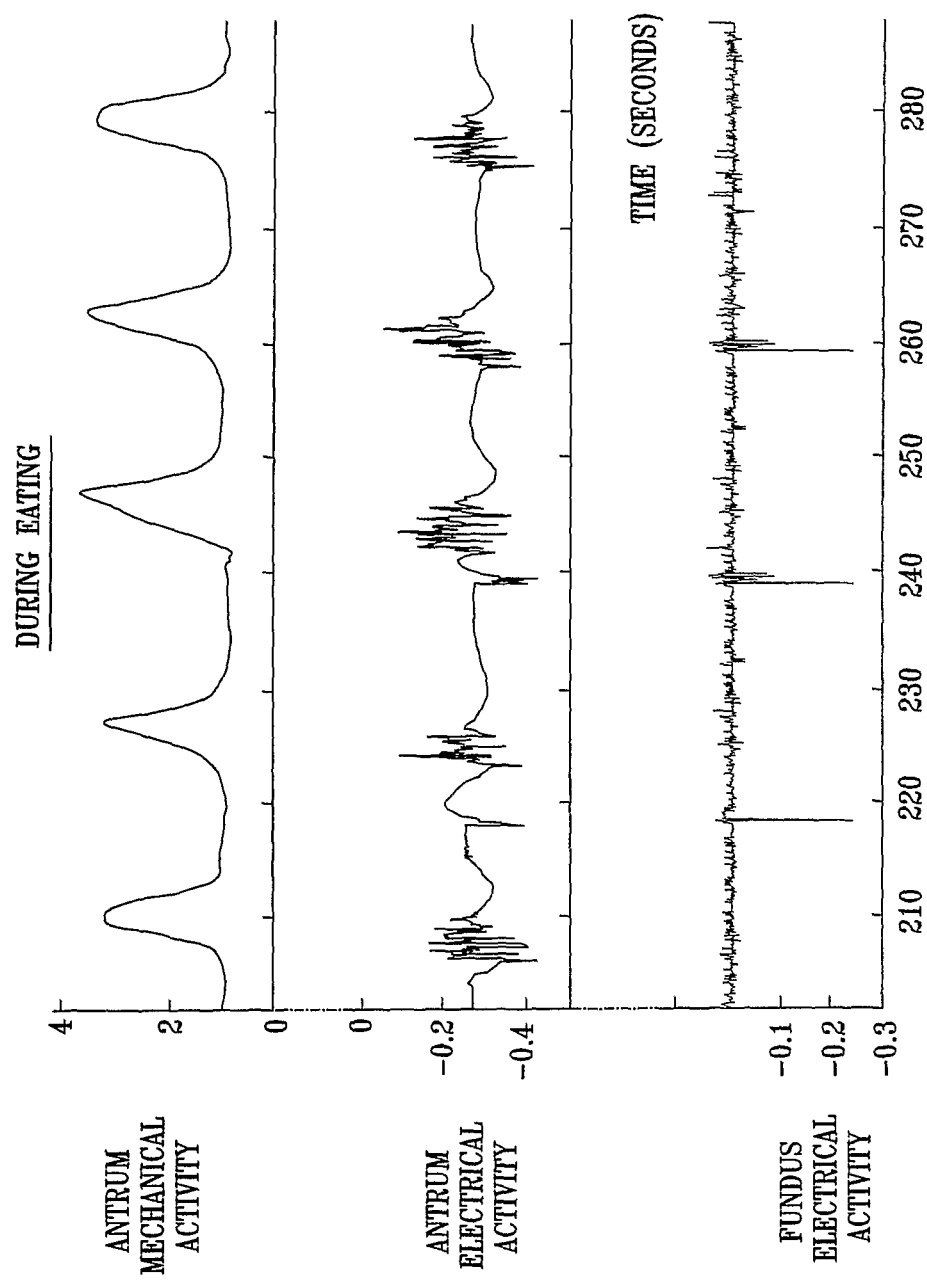

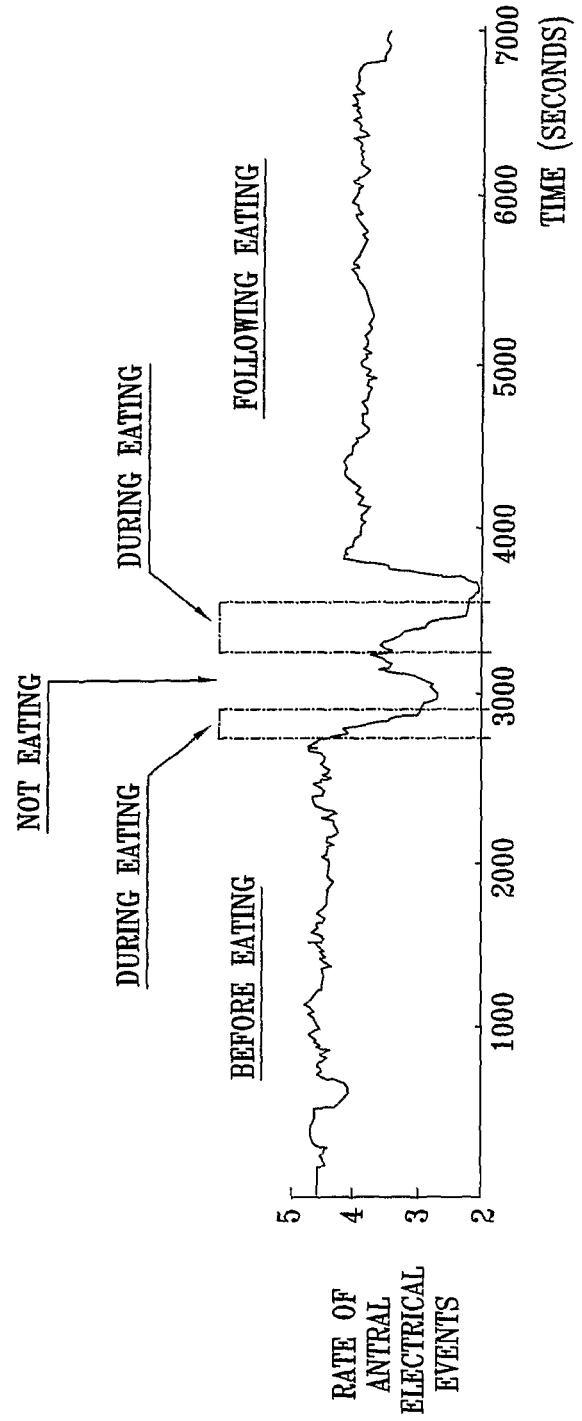

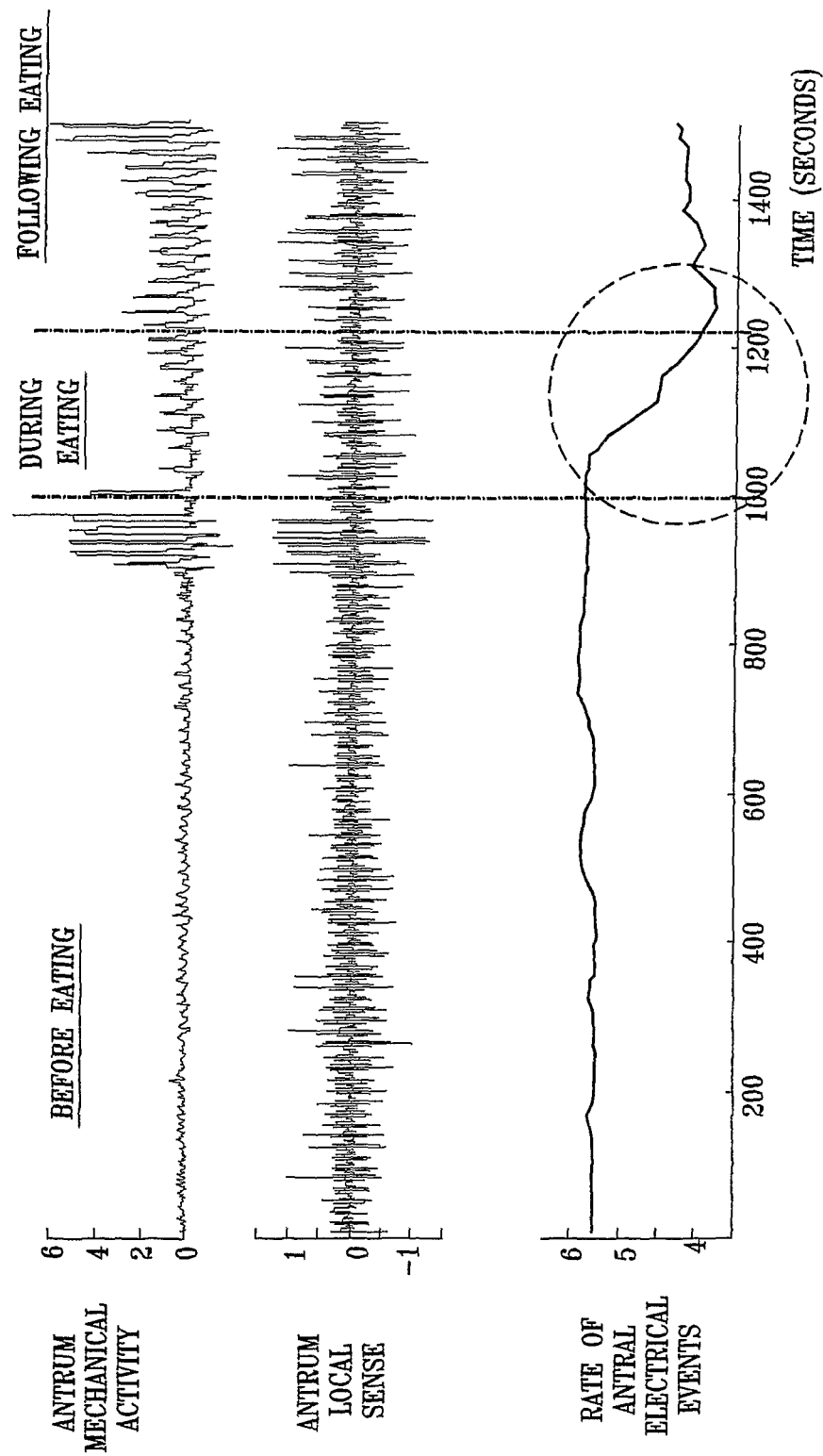

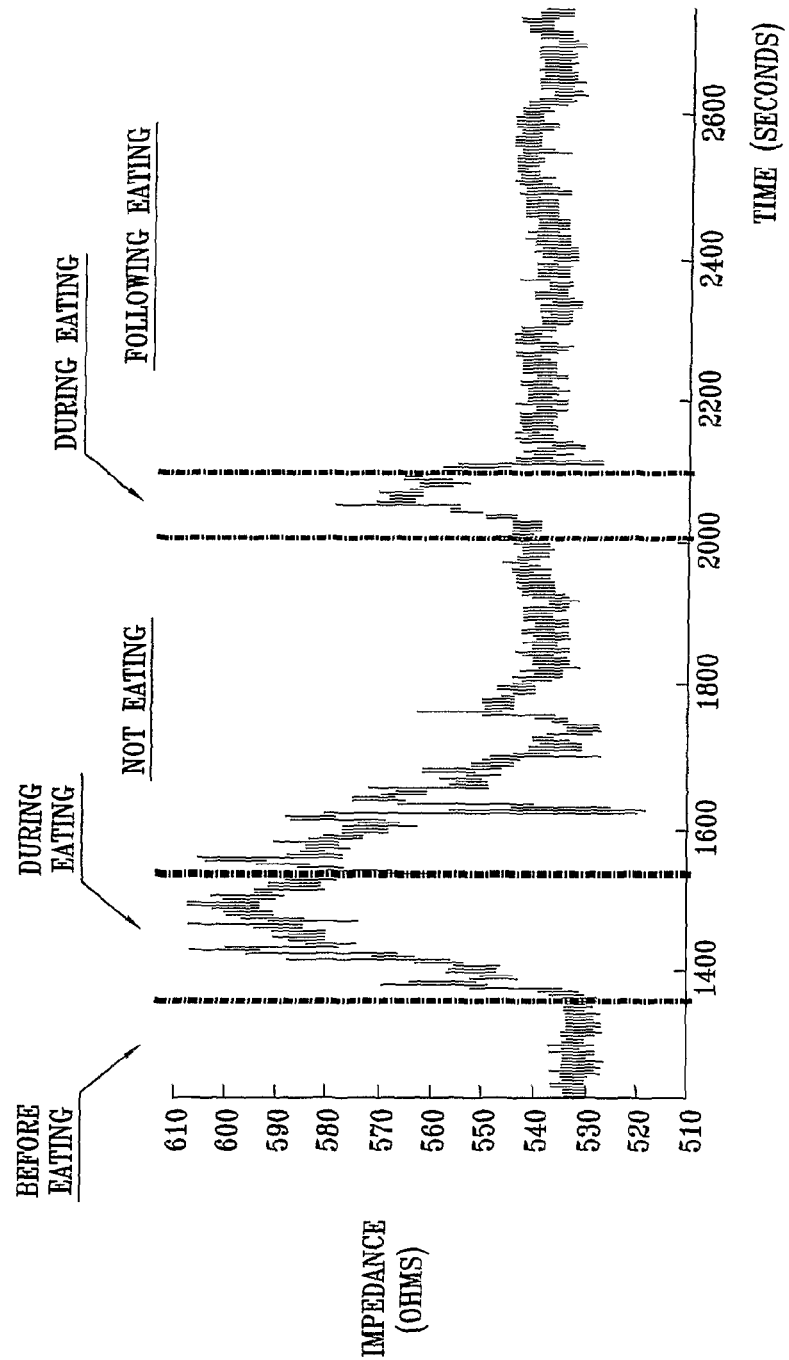

MONITORING, ANALYSIS, AND REGULATION OF EATING HABITS

CROSS-REFERENCES TO RELATED APPLICATIONS

The present application is a U.S. National Phase of PCT Application No. PCT/IL2005/000904 to Kliger et al., filed Aug. 18, 2005, which published as PCT Publication WO 06/018851, and which claims priority from U.S. Provisional Patent Application Ser. No. 60/602,550 to Kliger et al., filed Aug. 18, 2004, which are both incorporated herein by reference.

FIELD OF THE INVENTION

The present invention relates generally to tracking eating habits, and specifically to invasive techniques and apparatus for detecting and analyzing the swallowing and digesting of food.

BACKGROUND OF THE INVENTION

Obesity is a difficult to treat chronic condition defined by a body mass index (BMI=mass/height$^2$ [kg/m$^2$]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from obesity. Preferably, the invasive treatment is accompanied by changes in lifestyle, such as improved regulation of eating habits and an appropriate exercise regimen. Such lifestyle changes are dependent upon the self-discipline and cooperation of the patient.

A book entitled, *Textbook of Gastroenterology*, 3rd edition, edited by Yamada (Lippincott, Williams & Wilkins), which is incorporated herein by reference, has in Chapter 10 thereof a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com/transneuronix/Product/abstract.htm, which is incorporated herein by reference, describes techniques of electrical signal therapy designed to treat obesity.

U.S. Pat. No. 6,129,685 to Howard, which is incorporated herein by reference, describes apparatus and methods for regulating appetite by electrical stimulation of the hypothalamus and by microinfusion of an appropriate quantity of a suitable drug to a distinct site or region within the hypothalamus.

U.S. Pat. No. 4,823,808 to Clegg et al., which is incorporated herein by reference, describes a method for treating obesity, including receiving a physiological measurement and generating audio or visual feedback for the patient to hear or see. The feedback is used for purposes of teaching behavior modification.

U.S. Pat. No. 5,868,141 to Ellias, which is incorporated herein by reference, describes an endoscopic stomach insert for reducing a patient's desire to eat.

U.S. Pat. Nos. 6,067,991 to Forsell, 5,601,604 to Vincent, 5,234,454 to Bangs, 4,133,315 to Berman et al., 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese patient.

U.S. Pat. No. 5,690,691 to Chen et al., which is incorporated herein by reference, describes a gastric pacemaker for treating obesity and other disorders. The pacemaker includes multiple electrodes which are placed at various positions on the gastrointestinal (GI) tract, and deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another disorder.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, 6,026,326 to Bardy, and 3,411,507 to Wingrove, which are incorporated herein by reference, describe the application of electrical signals to the GI tract to treat various physiological disorders.

U.S. Pat. No. 5,979,449 to Steer, which is incorporated herein by reference, describes an oral appliance for appetite suppression.

U.S. Pat. No. 4,975,682 to Kerr et al., which is incorporated herein by reference, describes apparatus for food intake regulation which is external to the body and which is based upon the voluntary cooperation of the subject in order to be effective.

U.S. Pat. Nos. 5,861,014 to Familoni, 5,716,385 to Mittal et al., and 5,995,872 to Bourgeois, are incorporated herein by reference, and describe methods and apparatus for stimulation of tissue, particularly gastrointestinal tract tissue.

PCT Patent Publication WO 98/10830 to Ben-Haim et al., entitled, "Fencing of cardiac muscles," and U.S. patent application Ser. No. 09/254,903 in the national phase thereof, both of which are assigned to the assignee of the present patent application and are incorporated herein by reference, describe various methods for controlling the behavior of muscle tissue, for example by blocking or altering the transmission of signals therethrough.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described in the PCT Patent Publication with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

PCT Patent Publication WO 02/082968 to Policker et al., entitled, "Analysis of eating habits," which is assigned to the assignee of the present patent application and is incorporated herein by reference, describes apparatus and methods for detecting the occurrence of an eating event by a subject and analyzing the quantity and characteristics of the food ingested.

SUMMARY OF THE INVENTION

It is an object of some aspects of the present invention to provide apparatus and methods for detecting and tracking the swallowing of solids and liquids.

It is a further object of some aspects of the present invention to provide apparatus and methods for detecting, tracking, quantifying and determining the qualitative character of ingested liquids and solids.

It is still a further object of some aspects of the present invention to provide improved apparatus and methods for treating obesity.

It is yet a further object of some aspects of the present invention to provide apparatus and methods that enable the implementation of changes in food ingestion habits in a predictable and controlled manner.

It is an additional object of some aspects of the present invention to provide methods and apparatus for regulating food ingestion.

It is still an additional object of some aspects of the present invention to provide apparatus and methods for bariatric surgery that are less drastic than those currently employed.

In some embodiments of the present invention, apparatus for detecting, tracking, quantifying and determining the qualitative character of ingested liquids and solids comprises a sensor coupled to a patient's gastrointestinal tract. Typically, the sensor generates a signal indicative of the swallowing of food. An analysis module typically determines a quality of the food, for example, whether it is predominantly solid or liquid, and stores this information in an electronic memory. Alternatively or additionally, the analysis module determines other characteristics of the ingested material, for example, the nutritional, chemical, and/or caloric content. "Food," as used in the context of the present patent application and in the claims, is to be understood as including both solid and liquid food. Similarly, "eating," as used in the context of the present patent application and in the claims, is to be understood as being indicative of consumption of solids or liquids. "Swallowing," as used in the context of the present patent application and in the claims, is to be understood as being indicative of the onset of eating.

In some embodiments of the present invention, swallowing is detected by tracking the electrical activity in muscle tissue in the fundic region of the stomach. Typically, the commencement of enhanced electrical activity is also detected in muscle tissue in the antral region of the stomach. Measurement of the time delay between swallowing and the commencement of electrical activity in the antrum is typically used to differentiate between solid and liquid matter, which are generally passed at different rates through the stomach.

Alternatively or additionally, swallowing is detected by at least one sensor placed at a site on the gastrointestinal tract other than the fundic region of the stomach, and the sensor generates a signal indicative of swallowing. Appropriate sites include, but are not limited to, a site on the esophagus, a site on the stomach, and a site on the throat. Whenever detection of swallowing is described in the present patent application with respect to fundic activity, it is to be understood as being by way of example, and not as excluding detection by a sensor located elsewhere on the gastrointestinal tract.

Typically, measurement of the intensity and/or duration of the electrical activity in the antral region is correlated with aspects of fundic electrical activity denoting swallowing, as described hereinbelow, such that ingested matter of differing chemical and nutritional content can be distinguished. Further typically, the amount of food accumulated in the fundus or antrum is estimated by measuring a level of electrical activity at various sites in the stomach.

Typically, electrical activity response criteria of the stomach of an individual patient are determined and calibrated by measuring the response of the patient's stomach to various types of solid and liquid food. To ensure appropriate compliance, calibration is typically performed under the supervision of a healthcare worker. For illustration, a table such as the following may be established for a particular patient. Except with respect to the example of sugarless chewing gum, these illustrative values are shown with respect to a constant volume of food or liquid ingested (e.g., 100 ml of steak, water, or tomato juice).

TABLE I

| Substance | Fundic activity level | Antral activity level | Time delay until onset of antral activity |
|---|---|---|---|
| Sugarless chewing gum | 1 | 1 | — |
| Non-caloric liquid - Water | 2 | 1 | — |
| Caloric liquid - Tomato juice | 2 | 2 | <1 Minute |
| Caloric liquid - Milk | 2 | 2 | <1 Minute |
| Solid - Apple | 2 | 2 | Minutes |
| Solid - Meat | 2 | 3 | Minutes |

In this illustration, the measured data are typically analyzed to determine signal characteristics corresponding to the indicated fundic and antral electrical activity levels. For example, calibration of fundic activity during the chewing of sugarless gum typically yields a low level indication of swallowing, while calibration during the swallowing of liquids and solids yields a greater fundic response. Similarly, there is typically no significant antral response to the patient drinking water, while calibration during the digestion of liquids or solids having higher caloric content yields a greater antral response. Measurements are typically made of the delay time between swallowing and the commencement of antral activity, because consumption of liquids is typically characterized by a rapid transition from the fundus to the antrum, while solids typically stay in the fundus for at least about 10 minutes prior to being passed to the antrum. Typically, a large variety of liquids and solids are used to establish a profile of electrical response characteristics for each patient.

In some embodiments of the present invention, eating detection is accomplished by monitoring (a) the electrical impedance between two stomach sites and (b) the rate of the antral slow waves, whereby an eating event is indicated when both the impedance and the rate of the antral slow waves cross threshold values within a certain time period. The two stomach sites are typically but not necessarily located on a proximal portion of the stomach, such as the fundus. Leads used to measure the electrical impedance are typically bipolar leads. In an embodiment, in addition to or instead of monitoring electrical impedance and/or the rate of antral slow waves, eating detection is accomplished by monitoring mechanical changes indicative of gastric distension (e.g., using a sensor such as a strain gauge). Threshold values may be (a) generally predetermined, or (b) determined for each individual patient during a calibration process, in which the patient ingests various types of food while the impedance of the fundus and the rate of the antral slow waves are monitored, along with other relevant physiological data.

The threshold values indicating an eating event are typically updated to ensure accurate detection of eating by the patient. For some applications, the threshold values indicative of eating are modified through the use of a control unit that adapts the threshold values by checking that an indicated eating event corresponds to an actual eating event. Such checking may include relying on the patient to periodically verify or deny an eating event and/or through additional sensor information. For example, a repeated false positive indication of eating due to normal gastric activity would cause one or more of the threshold values used to signify an eating event to be modified.

Alternatively or additionally, the control unit is adapted to change one or more of the threshold values in response to a physiological event that has a tendency to cause false indications of eating activity. For example, a phenomenon known as the migrating motor complex (MMC) is characterized by a change in rhythm of antral electrical activity. This change in antral electrical activity is largely unrelated to eating, but can lead to false indications of eating activity. Since MMC activity lasts about 10 minutes and appears in a cyclical manner with a period of about 40 minutes, the control unit is adapted to identify MMC activity and respond, such that false positive identifications of eating activity are reduced. For example, when a change in antral electrical activity is detected, which may be indicative of eating, the control unit examines data on antral electrical activity from 30 to 50 minutes prior thereto, searching for similar activity that may be indicative of MMC activity. If the current activity is likely to be related to MMC activity, then the fundic threshold level signifying an eating event is increased during the subsequent times that are between 30 and 50 minutes in the future (i.e., when subsequent MMC activity is expected), thus reducing the likelihood of false positives relating to MMC contractions. As appropriate, other periodic physiological activities of the gastrointestinal system are treated in a similar manner. It is to be understood that the period of the MMC activity is described herein as being between 30 and 50 minutes by way of illustration and not limitation. In some patients, the period of the MMC activity may be higher, e.g., 50 to 90 minutes, or 90 to 120 minutes. For some applications, a calibration period is provided to determine the length of the period for each patient.

For some applications, various supplemental sensors are also applied to the gastrointestinal tract or elsewhere on or in the patient's body. These supplemental sensors, which may comprise pH sensors, blood sugar sensors, ultrasound transducers or mechanical sensors, typically convey signals to a control unit of the apparatus indicative of a characteristic of solids or liquids ingested by the patient. For example, an ultrasound transducer may be coupled to indicate whether ingesta are solid or liquid, and a pH sensor may indicate that an acidic drink such as tomato juice was consumed rather than a more basic liquid such as milk.

In some embodiments, the collected data are stored and intermittently uploaded to an external computer, typically by a wireless communications link, for review by the patient's physician, to enable monitoring of the patient's adherence to a dietary regimen.

For some applications, a specific schedule of allowed food ingestion is pre-programmed by the physician into the memory, and a processor is continuously operative to detect whether food consumption is taking place in accordance with the programmed schedule. For some patients, the schedule may be less strict with respect to drinking certain types of liquids, and more strict with respect to eating certain types of solid food. When an exception from the schedule is detected, the processor typically actuates a signal generator to convey an ingestion-control signal to the patient, in order to encourage the patient to adhere to the schedule. Typically, but not necessarily, apparatus and methods described in U.S. Provisional Patent Application 60/259,925, entitled, "Regulation of eating habits," filed Jan. 5, 2001, and in a PCT patent application entitled, "Regulation of eating habits," filed in January, 2002, both of which are assigned to the assignee of the present patent application and incorporated herein by reference, are utilized in the administration of the ingestion-control signal. Alternatively or additionally, the signal generator generates a visual, audio, or other cue or causes another reasonable discomfort to encourage the patient to adhere to the schedule.

For embodiments in which this form of dietary monitoring is supplemented by dietary regulation, the apparatus typically compares the indications of actual food and drink consumption with the pre-programmed schedule. In the event of a sufficient level of patient non-compliance, the ingestion-control signal is typically delivered to the patient's stomach via a set of electrodes placed in a vicinity thereof, so as to induce a sensation of discomfort or minor nausea. For example, an unpleasant sensation, such as nausea, may be induced by altering the natural electrical activity of the stomach, thereby inducing gastric dysrhythmia, or, alternatively, discomfort may be induced by pacing the rectus abdominus muscle.

Alternatively or additionally, the signal is applied to another site on or in the patient's body. For example, the ingestion-control signal may be applied mechanically or electrically in a vicinity of the cochlear nerve, so as to induce vertigo. Alternatively, the signal is applied so as to generate a brief pain sensation anywhere on the patient's body, which only recurs if the patient continues to eat. Further alternatively, the signal is applied to the esophagus or to the lower esophageal sphincter, so as to cause contraction of muscle tissue therein, thereby making any further eating difficult or very uncomfortable.

Alternatively or additionally, the ingestion-control signal is configured so as to induce a feeling of satiation, typically but not necessarily in accordance with methods described in U.S. patent application Ser. No. 09/734,358, which issued as U.S. Pat. No. 6,600,953, entitled, "Acute and Chronic Electrical Signal Therapy for Obesity," filed on Dec. 21, 2000, which is assigned to the Assignee of the present patent application and is incorporated herein by reference. For example, methods described in that application for engendering a feeling of satiation may be applied in conjunction with embodiments of the present invention, such that muscles in the vicinity of stretch receptors in the stomach are caused to contract, thereby resulting in decreased hunger sensations. Alternatively or additionally, the feeling of satiation is induced by applying electrical signals which enhance the mobility of chyme from the fundus to the antrum of the stomach, where stretch-receptor signals are generally generated to a greater extent for a given quantity of food than in the fundus.

In another embodiment, when an exception from the schedule of allowed food ingestion is detected, the processor typically conveys the exception to an external operator control unit, which in turn wirelessly communicates the exception in real time to a remote computer system. The remote computer system can be configured to analyze the exception based on predetermined rules and, if necessary, perform an appropriate action, such as notification of a healthcare worker, care provider, or family member of the patient, in order to encourage the patient to adhere to the schedule.

Typically, the schedule of allowed food ingestion can be modified after implantation of the apparatus, typically by means of a wireless communications link. In this manner, the schedule can be adjusted in response to changes in the patient's eating habits and experience with the apparatus.

In an embodiment, antral electrical activity of a subject is monitored, and a signal is applied to a vagus nerve of the subject in temporal coordination with the monitored antral electrical activity. For example, the signal may be applied during a slow wave as indicated by antral electrical or mechanical activity, or by other means. Alternatively or additionally, the signal is applied within 5 or 10 seconds before an anticipated slow wave, or within 5 or 10 seconds after a slow wave. As appropriate, this technique of vagus nerve stimulation may be coordinated, alternatively or additionally, with measurements of fundic impedance.

Typically, bursts of antral electrical activity occur several times a minute. In an embodiment, a signal is applied to the vagus nerve synchronized with each burst (e.g., (a) during the burst, (b) shortly following a defined feature of the burst, (c) prior to an anticipated feature of the burst, or (d) following a slow wave). For some applications, techniques described: (a) herein, (b) in the above-cited U.S. Pat. Nos. 5,188,104 and 5,263,480 to Wernicke et al., and/or (c) in the other references cited in the Background section of this application, are adapted for use in carrying out this embodiment of the present invention.

There is therefore provided, in accordance with an embodiment of the present invention, gastric apparatus, including:

a gastrointestinal sensor, adapted to be coupled to a gastrointestinal site of a subject and to generate a gastrointestinal sensor signal responsive to a property of the gastrointestinal site;

a set of one or more antral sensors, adapted to be coupled to an antral site of an antrum of the stomach and to generate an antral sensor signal responsive to a property of the antrum; and a control unit, adapted to receive and analyze the gastrointestinal and antral sensor signals, and to determine, responsive thereto, a characteristic of a food ingested by the subject.

Typically, the control unit is adapted to be implanted in the subject.

In an embodiment, the characteristic of the ingested food includes a caloric content of the ingested food, and the control unit is adapted to determine the caloric content. Alternatively or additionally, the characteristic of the ingested food includes a chemical content of the ingested food, and the control unit is adapted to determine the chemical content. Further alternatively or additionally, the characteristic of the ingested food includes a nutritional content of the ingested food, and the control unit is adapted to determine the nutritional content.

For some applications, the apparatus includes an operator unit, which is adapted to be disposed external to the subject and to transmit a control signal to the control unit.

In an embodiment, the gastrointestinal sensor is adapted to generate a swallowing sensor signal responsive to swallowing by the subject. Typically, the gastrointestinal sensor is adapted to be placed at an esophageal site of the subject, a site of the stomach of the subject, and/or a site of a throat of the subject.

Typically, the gastrointestinal sensor includes a set of one or more fundic sensors, adapted to be coupled to a fundic site of a fundus of the stomach of the subject and to generate a fundic sensor signal responsive to a property of the fundus, and the control unit is adapted to receive and analyze the fundic and antral sensor signals, and to determine, responsive thereto, the characteristic of the ingested food. In an embodiment, the fundic sensor set includes one or more strain gauges. Alternatively or additionally, the antral sensor set includes one or more strain gauges.

Typically, the fundic sensor set includes a set of fundic electrodes, adapted to generate a fundic electrode signal responsive to a property of the fundus, the antral sensor set includes a set of antral electrodes, adapted to generate an antral electrode signal responsive to a property of the antrum, and the control unit is adapted to receive and analyze the fundic and antral electrode signals, and to determine, responsive thereto, the characteristic of the ingested food. For example, the control unit may be adapted to determine, responsive to an analysis of at least one of the electrode signals, an amount of the ingested food accumulated in a region of the stomach. Alternatively or additionally, the control unit is adapted to count, responsive to an analysis of at least one of the electrode signals, a number of meals ingested by the subject during a period of time.

The antral electrode set typically includes two antral electrodes, adapted to be coupled to two sites of the antrum, and the control unit is adapted to identify a measure of electrical impedance between the two sites of the antrum. In this case, the control unit is typically adapted to determine the characteristic of the ingested food, responsive to a change in the measure of electrical impedance. For some applications, the fundic electrode set includes two fundic electrodes, adapted to be coupled to two sites of the fundus, and the control unit is adapted to identify a measure of electrical impedance between the two sites of the fundus. For example, the control unit may be adapted to determine the characteristic of the ingested food, responsive to a change in the measure of electrical impedance. Alternatively or additionally, the control unit is adapted to identify an increased measure of electrical impedance relative to a baseline value as indicative of eating. Further alternatively or additionally, the control unit is adapted to identify a substantial return towards a baseline value of the measure of electrical impedance as indicative of a termination of eating.

For some applications, the control unit is adapted to identify an increase in the measure of electrical impedance as indicative of an onset of eating. For example, the control unit may be adapted to detect the onset of eating, responsive to the increase in the measure of electrical impedance being greater than 5 ohms per centimeter of distance between the two sites of the fundus.

In an embodiment, the control unit is adapted to perform a calibration including measurement of a response of the fundic and antral electrode signals to ingestion by the subject of one or more test foods. For example, the one or more foods may include one or more solid foods, and the control unit may be adapted to perform the calibration responsive to ingestion of the one or more solid foods. Alternatively or additionally, the one or more foods includes one or more liquid foods, and the control unit is adapted to perform the calibration responsive to ingestion of the one or more liquid foods. Further alternatively or additionally, the one or more foods includes one or more solid foods and one or more liquid foods, and herein the control unit is adapted to perform the calibration responsive to ingestion of the one or more solid foods and the one or more liquid foods.

In an embodiment, the antral electrode set is adapted to generate the antral electrode signal responsive to an electrical potential change generated responsive to a contraction of a muscle of the antrum. In this case, the control unit is typically adapted to determine, responsive to an amplitude of the antral electrode signal, the characteristic of the ingested food. Alternatively or additionally, the control unit is adapted to determine, responsive to a frequency of the antral electrode signal, the characteristic of the ingested food. Further alternatively or additionally, the control unit is adapted to determine, responsive to a spike energy per antral cycle of electrical activity, the characteristic of the ingested food. Still further alternatively or additionally, the control unit is adapted to determine, responsive to a duration of the antral electrode signal, the characteristic of the ingested food.

In an embodiment, the control unit is adapted to determine, responsive to a change in a rate of antral electrode signal events, the characteristic of the ingested food. The control unit may alternatively or additionally be adapted to identify an increase in an amplitude of the antral electrode signal as indicative of an onset of a cephalic phase occurring in the subject. For some applications, the control unit is adapted to identify an increase in an amplitude of the antral electrode signal as indicative of an onset of antral digestion. Alternatively or additionally, the control unit is adapted to identify a reduction in a rate of antral electrode signal events as indicative of an onset of antral digestion.

For some applications, the control unit is adapted to identify an increased amplitude of the antral electrode signal relative to a baseline value as indicative of antral digestion. Alternatively or additionally, the control unit is adapted to identify a reduced rate of antral electrode signal events relative to a baseline value as indicative of antral digestion. Further alternatively or additionally, the control unit is adapted to identify a substantial return towards a baseline value of an amplitude of the antral electrode signal as indicative of a termination of antral digestion. Still further alternatively or additionally, the control unit is adapted to identify a substantial return towards a baseline value of a rate of antral electrode signal events as indicative of a termination of antral digestion.

The control unit is typically adapted to determine the characteristic of the ingested food, responsive to a time delay between an onset of eating and an onset of a decreased rate of electrical events in the antrum. For some applications, the control unit is adapted to determine the characteristic of the ingested food, responsive to the time delay and responsive to a threshold time delay. Alternatively or additionally, the control unit is adapted to determine, responsive to the time delay, an extent to which the ingested food includes solid food matter. In this case, the control unit is typically adapted to determine that the ingested food includes solid food matter, responsive to the time delay being more than about one minute. For some applications, the control unit is adapted to determine that the ingested food includes predominantly solid food matter, responsive to the time delay being more than about 5 minutes.

In an embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

For some applications, the control unit is adapted to determine the characteristic of the ingested food, responsive to a time delay between an onset of eating and an onset of increased electrical activity in the antrum. In this case, the control unit is typically adapted to determine the characteristic of the ingested food, responsive to the time delay and responsive to a threshold time delay. In an embodiment, the control unit is adapted to determine, responsive to the time delay, an extent to which the ingested food includes solid food matter. For example, the control unit may be adapted to determine that the ingested food includes solid food matter, responsive to the time delay being more than about one minute. Alternatively or additionally, the control unit may be adapted to determine that the ingested food includes predominantly solid food matter, responsive to the time delay being more than about 5 minutes. In an embodiment, the control unit is adapted to determine, responsive to the time delay, an extent to which the ingested food includes liquid food matter. For example, the control unit may be adapted to determine that the ingested food includes liquid food matter, responsive to the time delay being less than about 5 minutes. Alternatively or additionally, the control unit is adapted to determine that the ingested food includes predominantly liquid food matter, responsive to the time delay being less than about one minute.

Typically, the fundic electrode set is adapted to generate the fundic electrode signal responsive to an electrical potential change generated responsive to a contraction of a muscle of the fundus. For example, the control unit may be adapted to determine the characteristic of the ingested food responsive to an amplitude of the fundic electrode signal, a frequency of the fundic electrode signal, a duration of the fundic electrode signal, and/or a change in a rate of fundic electrode signal events of the fundic electrode signal.

In an embodiment, the control unit is adapted to identify an increased amplitude of the fundic electrode signal relative to a baseline value as indicative of eating. Alternatively or additionally, the control unit is adapted to identify an increased frequency of the fundic electrode signal relative to a baseline value as indicative of eating. Further alternatively or additionally, the control unit is adapted to identify a substantial return towards a baseline value of an amplitude of the fundic electrode signal as indicative of a termination of eating. Still further alternatively or additionally, the control unit is adapted to identify a substantial return towards a baseline value of a frequency of the fundic electrode signal as indicative of a termination of eating. For some applications, the control unit is adapted to identify an increase in an amplitude of the fundic electrode signal as indicative of an onset of eating. For example, the control unit may be adapted to detect the onset of eating responsive to the increase in the amplitude of the fundic electrode signal being greater than about 20 percent.

In an embodiment, the control unit is adapted to identify an increase in a frequency of the fundic electrode signal as indicative of an onset of eating. For example, the control unit may be adapted to detect the onset of eating, responsive to the increase in the frequency being greater than about 10 percent.

In an embodiment, the control unit includes a memory, adapted to store a result of the analysis performed by the control unit. Typically, the memory is adapted to upload the stored result to an external computer, e.g., by using a wireless communications link.

In an embodiment, the apparatus includes a supplemental sensor adapted to be placed at a site of the subject and to convey a supplemental sensor signal to the control unit. The control unit is typically adapted to receive and analyze the supplemental sensor signal, and to determine, responsive thereto, the characteristic of the ingested food. Alternatively or additionally, the control unit is adapted to receive and analyze the supplemental sensor signal, and to determine, responsive thereto, an onset of eating by the subject. Further alternatively or additionally, the control unit is adapted to receive and analyze the supplemental sensor signal, and to determine, responsive thereto, eating by the subject. Still further alternatively or additionally, the control unit is adapted to receive and analyze the supplemental sensor signal, and to determine, responsive thereto, a termination of eating by the subject. Typically, the supplemental sensor includes an electrode, a pH sensor, a blood sugar sensor, an ultrasound transducer, and/or a mechanical sensor. In an embodiment, the supplemental sensor is adapted to be placed at a gastrointestinal site of the subject, an esophageal site of the subject, a site of the stomach of the subject, and/or a site of a throat of the subject.

For some applications, the control unit includes a memory, adapted to store a schedule of allowed food ingestion, wherein the apparatus includes an operator unit, which is adapted to be disposed external to the subject, and wherein the operator unit is adapted to generate an external cue when the analysis performed by the control unit is indicative of the subject not eating in accordance with the ingestion schedule. For example, the external cue may include a visual cue, and the operator unit is adapted to generate the visual cue. Alternatively or additionally, the external cue includes an audio cue, and the operator unit is adapted to generate the audio cue. For some applications, the operator unit includes a user override, adapted to be used by the subject and adapted to disable the cue. Alternatively or additionally, the operator unit is adapted to modify the schedule stored in the memory. For example, the operator unit may be adapted to modify the schedule responsive to information obtained by the operator unit, e.g., via a wireless communications link.

In an embodiment, the apparatus includes a set of one or more current-application electrodes, adapted to be coupled to a tissue of the subject, and wherein the control unit is adapted to drive a current, responsive to the analysis, through the set of current-application electrodes into the tissue. For example, the current-application electrode set may be adapted to be placed at an aural site of the subject, at an esophageal site of the subject, and/or at a site of the stomach of the subject. For some applications, the control unit is adapted to drive the current into the tissue responsive to the characteristic of the ingested food. In an embodiment, the control unit is adapted to apply a pacing signal to a rectus abdominus muscle of the subject. For some applications, the control unit is adapted to drive the current into the tissue responsive to a time of the subject eating.

In an embodiment, the control unit is adapted to configure the current such that driving the current induces gastric dysrhythmia. Alternatively or additionally, the control unit is adapted to configure the current such that driving the current disrupts coupling of gastric mechanical activity and gastric electrical activity of the subject. Further alternatively or additionally, the control unit is adapted to configure the current such that driving the current induces a sensation of discomfort in the subject. Still further alternatively or additionally, the control unit is adapted to configure the current such that driving the current induces a sensation of nausea in the subject. Yet further alternatively or additionally, the control unit is adapted to configure the current such that driving the current induces a sensation of vertigo in the subject.

In an embodiment, the control unit is adapted to drive the current-application electrode set to apply an Excitable-Tissue Control (ETC) signal to the tissue. For example, the control unit may be adapted to drive the current-application electrode set to apply a stimulatory pulse at a site of application of the ETC signal. Alternatively or additionally, the control unit is adapted to drive the current-application electrode set to apply a stimulatory pulse to tissue at a site other than a site of application of the ETC signal. Still further alternatively or additionally, the control unit is adapted to drive the current-application electrode set to apply the ETC signal in order to increase an aspect of contraction of the tissue. For some applications, the control unit is adapted to drive the current-application electrode set to apply the ETC signal in order to cause tissue contraction in a first portion of the stomach of the subject, and stretching of a stretch receptor of the stomach in a second portion of the stomach. Alternatively or additionally, the control unit is adapted to drive the current-application electrode set to apply the ETC signal in order to increase a contraction strength of tissue in a vicinity of a stretch receptor of the stomach of the subject, so as to increase a sensation of satiation of the subject. Further alternatively or additionally, the control unit is adapted to drive the current-application electrode set to apply the ETC signal to the tissue so as to enhance movement of chyme from a fundus to the antrum of the stomach of the subject.

In an embodiment, the control unit includes a memory, adapted to store a schedule of allowed food ingestion, and wherein the control unit is adapted to withhold driving the current when the analysis performed by the control unit is indicative of the subject eating in accordance with the ingestion schedule. Typically, the ingestion schedule includes types of foods and associated amounts permitted during a time period, and the control unit is adapted to withhold driving the current when the analysis is indicative of the subject eating in accordance with the ingestion schedule. Alternatively or additionally, the ingestion schedule includes a number of meals permitted during a time period, and the control is adapted to withhold driving the current when the analysis is indicative of the subject eating in accordance with the ingestion schedule. Further alternatively or additionally, the ingestion schedule includes an amount of food permitted at a certain meal, and the control is adapted to withhold driving the current when the analysis is indicative of the subject eating in accordance with the ingestion schedule.

Typically, the memory is adapted to download a new schedule from an external computer. For some applications, the apparatus includes an operator unit, which is adapted to be disposed external to the subject and to transmit a control signal to the control unit. In an embodiment, the operator unit includes a user override, adapted to be used by the subject and adapted to withhold driving the current.

There is further provided, in accordance with an embodiment of the present invention, a method for analyzing gastric function of a stomach of a subject, including:

sensing a property of a gastrointestinal tract of the stomach;

sensing a property of an antrum of the stomach;

analyzing the property of the gastrointestinal tract and the property of the antrum; and determining, responsive to the analysis, a characteristic of a food ingested by the subject.

There is also provided, in accordance with an embodiment of the present invention, gastric apparatus, including:

one or more sensors, adapted to generate respective sensor signals responsive to activity of a gastrointestinal tract of a subject; and a control unit, adapted to:

receive and analyze the sensor signals, determine that an eating event has occurred, responsive to at least one of the sensor signals and a threshold, identify an aspect of at least one of the sensor signals deriving from rhythmic activity of the gastrointestinal tract that is not indicative of current eating by the subject, and modify the threshold responsive to the aspect of the signals that derives from activity that is not indicative of current eating.

In an embodiment, the control unit is adapted to modify the threshold if the aspect is indicative of a migrating motor complex (MMC).

In an embodiment:

in modifying the threshold, the control unit is adapted to modify the threshold in a threshold-modification direction, and the control unit is adapted, at a later time at least 30 minutes following modifying the threshold, to further modify the threshold in the threshold-modification direction responsive to identifying at the later time the aspect of the signals deriving from activity that is not indicative of current eating by the subject.

In an embodiment, the control unit is adapted, at a later time at least 30 minutes following modifying the threshold, to at least partially restore the threshold towards a previous value thereof, responsive to not identifying at the later time the aspect of the signals deriving from activity that is not indicative of current eating by the subject.

In an embodiment, the control unit is adapted to modify the threshold responsive to a relationship between a previous portion of the sensor signals and a current portion of the sensor signals.

In an embodiment, the control unit is adapted to modify the threshold responsive to the relationship, the previous portion being between about 30 and about 50 minutes prior to the current portion.

In an embodiment, the control unit is adapted to identify the previous portion of the sensor signals as being indicative of a migrating motor complex (MMC) and to identify the current portion of the sensor signals as being indicative of a MMC, and to modify the threshold responsive to identifying the previous and current portions as being indicative of the MMC.

There is additionally provided, in accordance with an embodiment of the present invention, apparatus, including:

a sensor, adapted to generate a signal responsive to antral electrical activity of a subject; and a vagus nerve stimulator, adapted to receive the signal and, responsive thereto, to stimulate a vagus nerve of the subject in temporal coordination with an aspect of the sensed signal.

There is still additionally provided, in accordance with an embodiment of the present invention, a selection method, including:

non-invasively recording a fasting electrogastrogram of a patient; and identifying the patient as a candidate for implantation of a medical device responsive to a rate of slow wave activity of the patient being greater than a threshold rate.

There is yet additionally provided, in accordance with an embodiment of the invention, a selection method, including:

recording a signal indicative of slow wave activity of a patient; and identifying the patient as a candidate for implantation of a medical device responsive to a rate of the slow wave activity of the patient being greater than a threshold rate.

In an embodiment, recording the signal includes non-invasively recording a fasting electrogastrogram of the patient.

In an embodiment, the threshold rate is at least 2.9 cycles per minute.

In an embodiment, identifying the patient includes identifying the patient as a candidate for implantation of a device capable of applying an ETC signal, responsive to the rate of slow wave activity being greater than the threshold rate.

In an embodiment, the method includes rejecting the patient as a candidate for implantation of the medical device responsive to the rate of slow wave activity being less than 2.9 cycles per minute.

The present invention will be more fully understood from the following detailed description of embodiments thereof, taken together with the drawings, in which:

BRIEF DESCRIPTION OF THE DRAWINGS

FIG. 3 is a graph showing a default fundus threshold value signifying an eating event, and modifications of the threshold value, in accordance with an embodiment of the present invention;

FIG. 4 is a schematic diagram showing experimental apparatus used to measure electrical responses to eating in the stomach of a normal rabbit, in accordance with a typical embodiment of the present invention;

FIG. 6A is a graph showing electrical activity in the fundus of a normal rabbit during and following eating, and results of analysis thereof, in accordance with a typical embodiment of the present invention;

FIG. 6B is a graph showing details of electrical and mechanical activity recorded during the taking of the data shown in FIG. 6A;

FIG. 9 is a graph showing the rate of electrical events in the antrum of a normal dog before, during, and after eating, and results of analysis thereof, in accordance with a typical embodiment of the present invention;

FIG. 10 is a graph showing electrical and mechanical activity and the rate of electrical events in the antrum of a normal dog before, during, and after eating, and results of analysis thereof, in accordance with a typical embodiment of the present invention; and FIG. 11 is a graph showing fundic electrical activity in a normal dog during several periods of eating and non-eating, and results of analysis thereof, in accordance with a typical embodiment of the present invention.

DETAILED DESCRIPTION OF EMBODIMENTS

Figure 1:
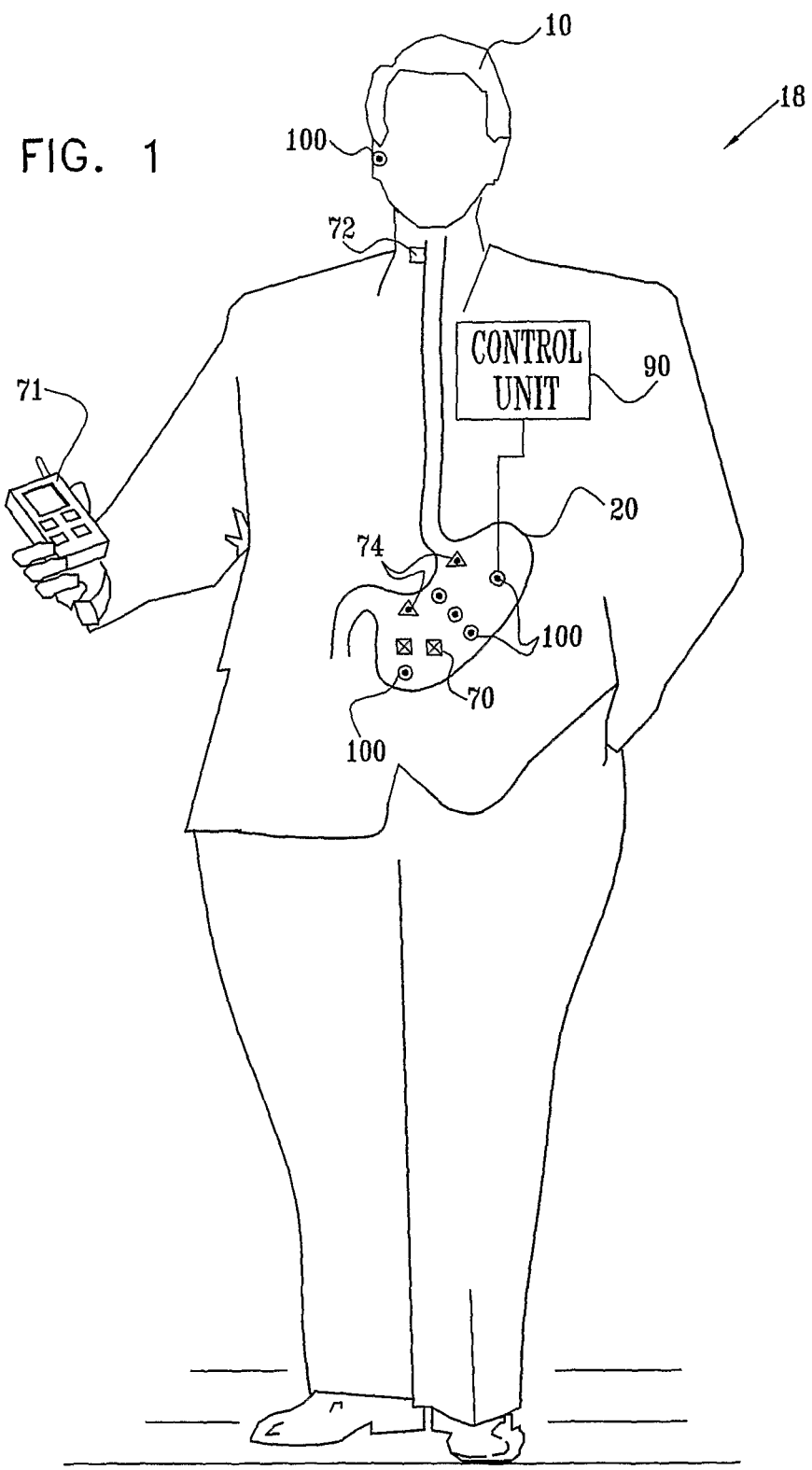
FIG. 1 is a schematic illustration of apparatus for treating obesity, in accordance with a typical embodiment of the present invention.

FIG. 1 is a schematic illustration of diet evaluation apparatus 18, which detects when a patient 10 swallows, and detects the type and amount of matter ingested, in accordance with a typical embodiment of the present invention. Typically, but not necessarily, apparatus 18 additionally determines, responsive to the detection, whether to apply electrical energy to modify the activity of tissue of patient 10. Apparatus 18 typically comprises mechanical sensors 70, supplemental sensors 72, local sense electrodes 74, operator controls 71, and one or more current-application electrodes 100.

Electrodes 74 and 100 are typically coupled to the serosal layer of a stomach 20 and/or inserted into the muscular layer of the stomach in the fundic and antral regions. Alternatively or additionally, the electrodes are coupled elsewhere on the stomach, gastrointestinal tract, or to other suitable locations in or on the patient's body. The number of electrodes and sensors, as well as the positions thereof, are shown in FIG. 1 by way of example, and other sites on stomach 20 or in or on the patient's body are appropriate for electrode and sensor placement in other applications of the present invention. Different types of electrodes known in the art are typically selected based on the specific condition of the patient's disorder, and may comprise stitch, coil, screw, patch, basket, needle and/or wire electrodes, or substantially any other electrode known in the art of electrical stimulation or sensing in tissue.

Typically, apparatus 18 is implanted in patient 10 in a manner generally similar to that used to implant gastric pacemakers or other apparatus for stimulating or sensing in the gastrointestinal tract that are known in the art. As appropriate, techniques described in one or more of the references cited in the Background section of the present patent application may be adapted for use with these embodiments of the present invention. Other methods and apparatus useful in carrying out some embodiments of the present invention are described in the above-cited U.S. Provisional Patent Application No. 60/259,925, entitled, "Regulation of Eating Habits," filed on Jan. 5, 2001, and in the above-cited PCT patent application and in the above-cited U.S. patent application Ser. No. 09/734,358, which issued as U.S. Pat. No. 6,600,953, entitled, "Acute and Chronic Electrical Signal Therapy for Obesity," filed on Dec. 11, 2000, which are assigned to the assignee of the present patent application and are incorporated herein by reference.

Figure 2:
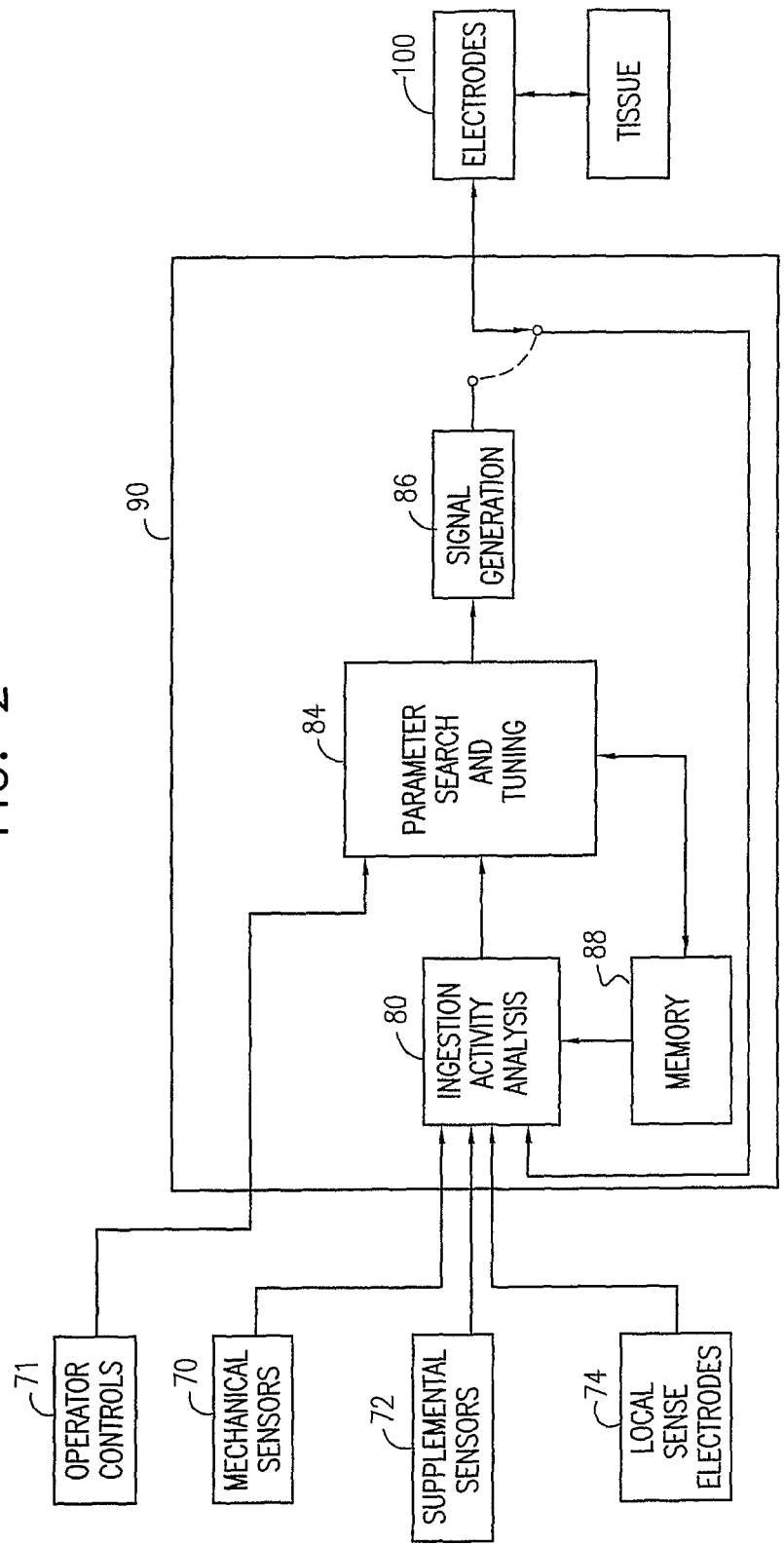
FIG. 2 is a schematic block diagram showing a control unit of the apparatus of FIG. 1, in accordance with a typical embodiment of the present invention.

FIG. 2 is a schematic block diagram illustrating details of operation of a control unit 90 of apparatus 18, in accordance with a typical embodiment of the present invention. Typically, control unit 90 is implanted in patient 10, and receives signals from mechanical sensors 70, supplemental sensors 72, and local sense electrodes 74, all of which are typically implanted on the gastrointestinal tract of the patient or elsewhere on or in the body of the patient. These sensors and electrodes are typically adapted to provide an "ingestion activity analysis" block 80 of the control unit with information about food ingestion and/or the present state of the stomach.

Typically, using techniques described hereinbelow, analysis block 80 determines each time that the patient swallows, and also the character and amount of the ingested matter. For example, local sense electrodes 74 coupled to the fundus of the stomach may send signals indicative of fundic electrical activity to analysis block 80, and analysis block 80 identifies aspects of these signals that are characteristic of swallowing of food by the patient. Additionally, mechanical sensors 70 and local sensor electrodes 74 coupled to the corpus and antral regions of the stomach typically send signals which analysis block 80 identifies as indicative of the onset, duration, and/or intensity of the digestive process in those regions. Typically, these data are utilized by analysis block 80 to determine a quality of the ingested matter, for example, whether it is predominantly solid or liquid. Alternatively or additionally, these data may be used to determine other characteristics of the ingested material, for example, its nutritional, chemical, and/or caloric content.

In a typical embodiment, analysis block 80 determines the time delay between swallowing (as measured, typically, by local sense electrodes 74 on the fundus) and the commencement of electrical and mechanical activity in the antrum. This delay is typically used to differentiate between the ingestion of solid and liquid matter, because solids are generally held in the fundus for at least about 10 minutes before being passed to the antrum, while liquids are generally passed to the antrum essentially immediately.

Alternatively or additionally, the amount of food accumulated in the various regions of stomach 20 is estimated by measuring a level of electrical or mechanical activity in a vicinity of those regions. For example, in some embodiments of the present invention, eating detection is accomplished by monitoring the impedance of the fundus and the rate of the antral slow waves, whereby an eating event is indicated when both the impedance of the fundus and the rate of the antral slow waves cross threshold values within a certain time period.

Further alternatively or additionally, analysis block 80 processes data from supplemental sensors 72 indicative of the blood sugar level of the patient, to enable an evaluation of whether and of what type of food has been ingested.

In order to improve the accuracy of the analyses described hereinabove, analysis block 80 is typically calibrated by measuring the appropriate electrical response criteria of stomach 20 of patient 10 to various types of solid and liquid food.

For some applications, analysis block 80 stores the results of its analysis in a memory block 88 of control unit 90, and these results are later uploaded to an external computer, typically by a wireless communications link, for review by the patient's physician. Alternatively or additionally, analysis block 80 conveys results of its analysis of the inputs from mechanical sensors 70, supplemental sensors 72, and local sense electrodes 74, to a "parameter search and tuning" block 84 of control unit 90. The parameter search and tuning block adapts the threshold values indicative of eating by checking that an indicated eating event corresponds to an actual eating event. For example, the parameter search and tuning block may rely on the patient to periodically verify or deny an eating event by using operator control 71. Alternatively or additionally, the parameter search and tuning block utilizes additional sensor information such as antrum impedance, which varies during eating while remaining steady in the absence of eating. In an embodiment, a false positive indication of an eating event may cause one or more of the threshold values to be increased, while a false negative may cause one or more of the threshold values to be decreased.

Alternatively or additionally, search and tuning block 84 is adapted to change one or more of the threshold values in response to a physiological event that has a tendency to cause false indications of eating activity. For example, the migrating motor complex (MMC) is characterized by increased antral electrical activity, which can lead to false indications of eating activity. Since MMC activity lasts about 10 minutes and appears in a cyclical manner with a time lag of about 40 minutes between events, the search and tuning block is adapted to identify MMC activity and respond, such that false positive identifications of eating activity are reduced.

In an embodiment, a calibration period is provided in which a record is generated of actual eating events by the subject. As appropriate, the calibration period may be about one day, several days, or longer than a week. The record of actual eating events may comprise, for example, entries made by the subject or another person in an electronic or non-electronic journal, or using other techniques known in the art for detecting swallowing or otherwise detecting eating. In this embodiment, thresholds for fundic impedance and antral electrical activity are set responsive to (a) the record of actual eating events and (b) measurements of fundic impedance and antral electrical activity made during the calibration period. Typically (but not necessarily), some preference is given to reducing false negatives relative to reducing false positives. In other words, for many applications, it is more important to avoid missing a detection of an eating event than to avoid incorrectly reporting that an eating event occurred. (For other applications, both are of equal importance, or the latter is more important.)

In an embodiment, two parallel matrices are generated in response to the record of actual eating events and the measurements of fundic impedance and antral electrical activity made during the calibration period. The first matrix, a false negative matrix, has a range of thresholds for changes in fundic impedance on the x-axis of the matrix, and a range of antral electrical activity on the y-axis of the matrix. For clarity of description (although not necessarily in practice), the range of fundic impedance extends from normalized values of 1 to 20, and the range of antral electrical activity also extends from 1 to 20. The false negative matrix is then generated as a 20×20 matrix. Each cell in the false negative matrix represents a given combination of possible thresholds of fundic impedance and antral electrical activity. The value stored in a given cell represents a value associated with the extent of false negatives that would have been generated for the given fundic impedance threshold and antral electrical activity threshold represented by that cell. For example, if a normalized fundic impedance threshold of 2 and a normalized antral electrical activity threshold of 7 yielded no false negatives during the calibration period, then the value of the false negative matrix at cell (2, 7) would be zero. Similarly, if a normalized fundic impedance threshold of 20 and a normalized antral electrical activity value of 20 did not result in an identification of any of several actual eating events during the calibration period, then the value of the false negative matrix at cell (20, 20) would be 100%. For some applications, the value of a given cell in the false negative matrix is defined as: 1−(number of correct detections/number of actual eating events).

A corresponding false positive matrix is generated. The x-axis and y-axis of the false positive matrix are analogous to the corresponding axes of the false negative matrix. Typically, the value in each cell of the false positive matrix reflects the total or average number of false positive indications of eating in a given time period (e.g., one day, or throughout the calibration period).

A calibration period analysis algorithm typically identifies one or more near-minimum values in the false negative matrix. These near-minimum values (NMV's) typically are located in one or more "clouds" on the false negative matrix. Similarly, the calibration period analysis algorithm typically identifies one or more NMV's in the false positive matrix. (The term "near-minimum value" is understood to include actual minimum values, as well.) The near-minimum values are typically located in one or more clouds on the false positive matrix, as well. For some applications, in order to determine a suitable fundic impedance threshold and a suitable antral electrical activity threshold for use during regular operation of an eating detection algorithm, the calibration period analysis algorithm first identifies cells in the false negative matrix that are NMV's, and then determines which of the corresponding cells in the false positive matrix are also NMV's.

In some cases, only a single set of fundic impedance and antral electrical activity threshold values (x, y) is an NMV in both the false negative and the false positive matrix. In these cases, this set typically defines the thresholds for use in regular operation of the eating detection algorithm.

In other cases, multiple sets (x(i), y(i)) of thresholds are identified that correspond to an NMV in both the false negative matrix and the false positive matrix. In these cases, for some applications, the calibration period analysis algorithm determines one of the multiple threshold sets that is likely to have a high level of "stability" during regular operation of the eating detection algorithm. To determine stability, the calibration period analysis algorithm typically determines which cell in the false negative matrix having an NMV is not adjacent to or relatively near to one or more cells in the false negative matrix having relatively high values (i.e., indicating many false negatives).

For example, one cell (x1, y1) in the false negative matrix having an NMV of 5% may be relatively near to a second cell (x1−1, y1+2) having an NMV of 30%. Another cell (x2, y2) in the false negative matrix having an NMV of 5% may have no cells within +/−2 on the x-axis or the y-axis having an NMV greater than 25%. In this case, the fundic impedance and antral electrical activity thresholds represented by the second cell would be selected by the calibration period analysis algorithm.

In another example, a summing algorithm typically weighted by proximity is used to evaluate the neighborhood (e.g., +/−3 cells) of all cells having an NMV. The cell that is both NMV and having the lowest "false negative sum" for its neighborhood is selected by the calibration period analysis algorithm to represent the fundic impedance and antral electrical activity thresholds during regular operation of the eating detection algorithm.

For some applications, the stability determination described hereinabove is performed with respect to values in the false positive matrix or with respect to values in both the false positive matrix and the false negative matrix.

In an embodiment, if the calibration period analysis algorithm identifies n cells having stable NMV's in both the false negative and false positive matrices, then during regular operation of the eating detection algorithm, an evaluation of each of the corresponding n sets of fundic impedance and antral electrical activity thresholds is performed. A determination of an eating event is made responsive to some or all of the n sets of thresholds (e.g., responsive to the measured fundic impedance and antral electrical activity exceeding the corresponding thresholds of ½ of the n sets).

Table II and Table III (below) display results obtained based on an experiment with an obese human patient having (a) electrodes implanted on the fundus, for measuring fundic impedance, and (b) electrodes implanted on the antrum, for measuring the rate of antral electrical activity, in accordance with an embodiment of the present invention. During an approximately six hour monitoring period, the patient was free to eat whatever she chose, whenever she chose to eat. During this period, the patient recorded eating three times (pizza bread at 09:45, pasta with cheese at 12:30, and candy at 14:30).

TABLE II

Sample false negative matrix

|    | 18   | 18.5 | 19   | 19.5 | 20   | 20.5 | 21   | 21.5 | 22   | 22.5 | 23  |
|----|------|------|------|------|------|------|------|------|------|------|-----|
| 10 | 33   | 33   | 33   | 33   | 33   | 33   | 33   | 33   | 33   | 67   | 67  |
| 12 | 33   | 33   | 33   | 33   | 33   | 33   | 33   | 33   | 33   | 67   | 67  |
| 14 | 33   | 33   | 33   | 33   | 33   | 33   | 33   | 33   | 33   | 67   | 67  |
| 16 | 33   | 33   | 33   | 33   | 33   | 33   | 33   | 33   | 33   | 67   | 67  |
| 18 | 33   | 33   | 33   | 33   | 33   | 33   | 33   | 33   | 33   | 67   | 67  |
| 20 | 33   | 33   | 33   | 33   | 33   | 33   | 33   | 33   | 33   | 67   | 67  |
| 22 | 33   | 33   | 33   | 33   | 33   | 33   | 33   | 33   | 33   | 67   | 67  |
| 24 | 33   | 33   | 33   | 33   | 33   | 33   | 33   | 33   | 33   | 67   | 67  |
| 26 | 33   | 33   | 33   | 33   | 33   | 33   | 33   | 33   | 33   | 67   | 67  |
| 28 | 33   | 33   | 33   | 33   | 33   | 33   | 33   | 33   | 33   | 67   | 67  |
| 30 | [33] | [33] | [33] | [33] | [33] | [33] | [33] | [33] | [33] | 67   | 67  |
| 32 | [33] | [33] | [33] | [33] | *33* | [33] | [33] | [33] | [33] | 67   | 67  |
| 34 | [33] | [33] | [33] | [33] | [33] | [33] | [33] | [33] | [33] | 67   | 67  |
| 36 | [33] | [33] | [33] | [33] | [33] | [33] | [33] | [33] | [33] | 67   | 67  |
| 38 | [33] | [33] | [33] | [33] | [33] | [33] | [33] | [33] | [33] | 67   | 67  |
| 40 | 67   | 67   | 67   | 67   | 67   | 67   | 67   | 67   | 67   | 100  | 100 |
| 42 | 67   | 67   | 67   | 67   | 67   | 67   | 67   | 67   | 67   | 100  | 100 |
| 44 | 100  | 100  | 100  | 100  | 100  | 100  | 100  | 100  | 100  | 100  | 100 |
| 46 | 100  | 100  | 100  | 100  | 100  | 100  | 100  | 100  | 100  | 100  | 100 |

TABLE III

Sample false positive matrix

|    | 18  | 18.5 | 19  | 19.5 | 20  | 20.5 | 21  | 21.5 | 22  | 22.5 | 23 |
|----|-----|------|-----|------|-----|------|-----|------|-----|------|----|
| 10 | 7   | 7    | 7   | 6    | 6   | 4    | 4   | 4    | 4   | 4    | 4  |
| 12 | 5   | 5    | 5   | 5    | 5   | 4    | 4   | 4    | 4   | 4    | 4  |
| 14 | 4   | 4    | 4   | 4    | 4   | 3    | 3   | 3    | 3   | 3    | 2  |
| 16 | 3   | 3    | 3   | 3    | 3   | 3    | 3   | 3    | 3   | 3    | 2  |
| 18 | 3   | 3    | 3   | 3    | 3   | 3    | 3   | 3    | 3   | 3    | 2  |
| 20 | 2   | 2    | 2   | 2    | 2   | 2    | 2   | 2    | 2   | 2    | 1  |
| 22 | 2   | 2    | 2   | 2    | 2   | 2    | 2   | 2    | 2   | 1    | 1  |
| 24 | 1   | 1    | 1   | 1    | 1   | 1    | 1   | 1    | 1   | 1    | 1  |
| 26 | 1   | 1    | 1   | 1    | 1   | 1    | 1   | 1    | 1   | 1    | 1  |
| 28 | 1   | 1    | 1   | 1    | 1   | 1    | 1   | 1    | 1   | 1    | 1  |
| 30 | [0] | [0]  | [0] | [0]  | [0] | [0]  | [0] | [0]  | [0] | 0    | 0  |
| 32 | [0] | [0]  | [0] | [0]  | *0* | [0]  | [0] | [0]  | [0] | 0    | 0  |
| 34 | [0] | [0]  | [0] | [0]  | [0] | [0]  | [0] | [0]  | [0] | 0    | 0  |
| 36 | [0] | [0]  | [0] | [0]  | [0] | [0]  | [0] | [0]  | [0] | 0    | 0  |
| 38 | [0] | [0]  | [0] | [0]  | [0] | [0]  | [0] | [0]  | [0] | 0    | 0  |
| 40 | 0   | 0    | 0   | 0    | 0   | 0    | 0   | 0    | 0   | 0    | 0  |
| 42 | 0   | 0    | 0   | 0    | 0   | 0    | 0   | 0    | 0   | 0    | 0  |
| 44 | 0   | 0    | 0   | 0    | 0   | 0    | 0   | 0    | 0   | 0    | 0  |
| 46 | 0   | 0    | 0   | 0    | 0   | 0    | 0   | 0    | 0   | 0    | 0  |

An experiment-analysis algorithm was set to have a "refractory" period of 30 minutes following each detection of eating, during which a new detection of eating would not be registered. A "hysteresis" period of 8 minutes was set, whereby a detection of eating would only be made if fundic impedance and antral electrical activity passed respective thresholds within 8 minutes of each other. Lastly, an identified eating detection was counted as being a true eating detection if it occurred within 15 minutes prior to or following the time of eating as recorded by the patient.

The x-axis in Table II (and Table III) represents threshold rates of antral electrical activity, in minutes. The y-axis represents fundic impedance, in ohms. Thus, for example, Table II shows that if the threshold for antral electrical activity were set at 19 seconds (such that only antral electrical activity occurring slower than once every 19 seconds generates an indication of potential eating), and if the threshold for fundic impedance change were set at 16 ohms (such that an indication of potential eating is only generated if the fundic impedance increases by more than 16 ohms), then two actual eating events would have been correctly detected, and one actual eating event would not have been detected. This defines a false negative percentage of 33%.

Similarly, in Table III, the total number of false positive indications of eating are shown in the matrix as a function of particular threshold settings. For example, for a fundic impedance threshold of 19 ohms, and an antral electrical activity threshold rate of 21 seconds, no false positive indications of eating were generated.

Cells in each matrix were automatically analyzed to determine optimal or near-optimal threshold settings for use in regular operation of an eating detection algorithm. Suitable thresholds optimizing both the fundic impedance threshold and the antral electrical activity rate threshold are marked by cells having square brackets surrounding their values. Thus, for this patient, it was found that a fundic impedance threshold ranging from 30 to 38 ohms and an antral electrical activity rate threshold ranging from 18 to 22 seconds is generally optimal. A particular threshold set (32 ohms, 20 seconds) was identified by the automated analysis as being particularly stable (in addition to minimizing false positive and false negative indications), and is marked by a "*".

In an embodiment, the following algorithm and/or pseudocode is executed to determine the fundic impedance and antral electrical activity thresholds. Typically, the identified user would be a physician reviewing records of actual eating events ("bookmarks") and measured data.
 1. Input session
   1. User chooses files of data.
   2. For each selected file, allow the user to review the bookmarks and have the following options:
     i. remove/approve each bookmark
     ii. accept all bookmarks without reviewing
     iii. add a bookmark (e.g., to represent an actual eating event not previously recorded)
     iv. impose a fixed time shift on all bookmarks (e.g., in case the "time stamps" of the bookmarks are not aligned with the time stamps of measurements of fundic impedance 3. The user will then select the following detection criteria ranges or approve the default:
   i. Time before and after a meal bookmark that will be considered as a true detection, if detected (default: +/−15 min)
   ii. Time before and after a meal that will not be considered as a false detection, if a detection is made (default: from 15 min before bookmark to 45 min after bookmark)
2. For all possible rate and impedance thresholds:
   Find all "eating detection events," i.e., times during which both the fundic impedance and the rate of slow waves cross their corresponding thresholds in a common time frame, typically 3-10 minutes
   Calculate false negative percentage (FN) (percentage of meals that did not have a detection within the pre-defined "true detection time limits"
   Calculate false positives per day (FP) (number of detections that did not correspond to an actual eating event, i.e., a bookmark, within the pre-defined "false detection range," divided by the number of days).
3. Identify the "optimal set" of thresholds combination according to the following rule:
   1. Find all threshold pairs (fundic impedance/rate of antral electrical activity) that generate the minimal (or near minimal) false negative percentage.
   2. In this set of threshold pairs, find the corresponding subset with minimal false positives per day. The results of these two steps are defined as the "optimal set"
4. Find closed spaces of points in the optimal set:
   i. Set cloud number=1
   ii. Unmark all points in the optimal set
   iii. Find the unmarked point in the optimal set that has minimal value of F and R values: $\min_{r,f}\{P(r,f): P \in \text{optimal set}\}$ and mark it
   iv. Set Rcount=1; Fcount=0;
   v. If P(r+count,f+Fcount)∈optimal set then
      1. mark P(r+Rcount; f+Fcount)
      2. Increment Rcount
      3. goto (iv)
      else
         if there is an unmarked point in the range P(r:r+1, f:f+1) that belongs to the optimal set then
            1. set Rcount and Fcount so that r+Rcount and f+Fcount will point to that pair
            2. mark the selected pair
            3. goto iv
            else
               1. set cloud_number=cloud_number+1
               2. define a set cloud(cloud_number) and assign all marked points from the optimal set to it
               3. remove all marked points from the optimal set
               4. goto (iii)
5. Find cloud's edges
   1. set $P=\min_{r,f}\{P(r,f):P \in \text{cloud}\}$
   2. set count=1
   3. Unmark all F/R matrix members
   4. set $E(\text{count})=\min_{R_{count}}(P(r+R\text{count},f) \notin \text{cloud})$
   5. mark E(count)
   6. in the range $P(R_{E(count)} \pm 1, F_{E(count)} \pm 1)$ find an unmarked point $P \notin \text{cloud}$ for which the set $N(R_P \pm 1, F_P \pm 1) \in \text{cloud}$ is not empty
   7. If P exists then
      a. Set count=count+1
      b. Set E(count)=P
      c. Goto 5
   Else
      a. in the range $P(R_{E(1)} \pm 1, F_{E(1)} \pm 1)$ find an unmarked point $P \notin \text{cloud}$ for which the set $N(R_P \pm 1, F_P \pm 1) \in \text{cloud}$ is not empty
      b. if P exists then
         1. Set count-count+1
         2. Set E(count)=P
         3. Goto 5
      d. Else check if E(1) and E(count) are neighbors
      e. If they are neighbors, then goto 6 else create a set of additional points for the set E according to the following rules:
         1. the number of the points will equal max(abs $(R_{E(1)}-R_{E(count)})$, abs$(F_{E(1)}-F_{E(count)}))$
         2. Each new point will have the FN, FP values of the opposite edge point
6. Grade each point in each cloud
   1. For each cloud
   2. for each P∈cloud
   3. grade(P)=0
   4. for each $E_{count}$ point in E
   5. grade(P)=grade(P)+(FN($E_{count}$)+FP($E_{count}$)/4)/dist(P,$E_{count}$)
7. Choose the 3 points with minimal grade.
8. Offer these three combinations to the user, and specify for each of them the values of false negative and false positive it generates.

FIG. 3 is a graph showing an example of a change in a sensing threshold value during suspected periods of MMC activity, in accordance with an embodiment of the present invention. Time period B indicates a time when increased antral electrical activity is detected, which may be indicative of either eating or MMC activity. Search and tuning block 84 then examines data indicating antral electrical activity from 30 to 50 minutes prior to the present activity (i.e., around time A) to determine whether similar activity occurred at time A. If similar activity occurred at time A, the present activity during time period B is of increased likelihood to be related to MMC activity. Therefore, as shown in FIG. 3, the fundus threshold level is increased during time period B, thus reducing the likelihood of false positives relating to MMC activity. In this manner, fundus impedance levels measured prior to time period B generally only need to exceed the default value shown in FIG. 3 in order to produce an indication of eating. Fundus impedance levels during time period B, however, typically need to exceed the elevated threshold in order to produce an indication of eating. Typically, the fundus threshold value is further increased in a subsequent time period C, 30 to 50 minutes after time period B, if antral electrical activity is high during period C, as this is evidence of likely MMC activity. For some applications, other periodic physiological activity of the gastrointestinal tract is treated in a similar manner.

In some other embodiments of the present invention, eating detection is accomplished by monitoring the rate of antral electrical events. Results described hereinbelow show that the rate of antral electrical events typically decreases upon the commencement of eating. For some applications, the reduction of antral electrical events is used in addition to or instead of the techniques described hereinabove for the identification of eating activities. Combining several detection criteria for the onset of eating is typically used to reduce the number of false positives and false negatives.

In an embodiment, the standard deviation of the values of event-to-event time differences are evaluated in a given sliding time window. As appropriate, the events can be detection of electrical activity or mechanical activity in the antrum. The length of the sliding time frame is typically between about 20 seconds and about 2 minutes, but, as appropriate, can be between about 20 seconds and about 10 minutes. In order to detect eating, the measured data are evaluated so as to identify a single event-to-event time difference which is more that 2-3 times the standard deviation of the former events.

With reference to FIG. 2, block 84 evaluates the analysis performed by analysis block 80 with respect to a pre-programmed or variable ingestion schedule stored in memory block 88, so as to determine whether the patient is eating in compliance with a schedule. Typically, the schedule can be modified after implantation of control unit 90, by communication from operator controls 71 using methods described hereinbelow. If it is determined that the patient's eating is not in compliance with the schedule (e.g., the patient has eaten too much at one meal, or has eaten too many meals in a day, or has had too much of a certain type of food or drink), then block 84 typically actuates a signal generator block 86 to generate electrical signals that are applied by current-application electrodes 100 to tissue of patient 10. Block 86 typically comprises amplifiers, isolation units, and other standard circuitry known in the art of electrical signal generation.

The signals generated by block 86 are typically configured so as to induce a response appropriate for controlling the patient's eating habits. For example, block 86 may drive current-application electrodes 100 to apply signals to the stomach that induce gastric dysrhythmia and the resultant feeling of discomfort or nausea. Alternatively or additionally, the signals are applied to an aural site of patient 10 (e.g., in a vicinity of the cochlear nerve or the tympanic membrane), and are configured to induce vertigo, or another unpleasant balance-related sensation. Alternatively or additionally, block 86 generates a visual, audio, or other cue to encourage the patient to adhere to the schedule.

For some applications, control unit 90 drives electrodes 100 to apply a modulation signal to muscle in one area of stomach 20, so as to induce a contraction of the stimulated muscle that, in turn, induces satiety when food in an adjacent area of the stomach causes additional stretching of stretch-receptors therein. This signal may be applied in addition to or instead of the signals described hereinabove that produce gastric or other discomfort. The form of contraction-mediated stretching utilized in these applications simulates the normal appetite-reduction action of the stomach's stretch-receptors, without the patient having eaten the quantities of food which would normally be required to trigger this appetite-reduction response. In a typical application, current-application electrodes 100 are placed around the body of the stomach and are driven to induce a generally steady-state contraction of the corpus, which simulates electrically the squeezing of the corpus produced mechanically by implanted gastric bands known in the art. Alternatively or additionally, the sensation of satiety occurs in response to changes in slow wave propagation induced by the modulation signal, or in response to another physiological phenomenon.

Typically, the signals applied by current-application electrodes 100 include, as appropriate, an Excitable-Tissue Control (ETC) signal and/or an excitatory signal that induces contraction of muscles of the stomach. Aspects of ETC signal application are typically performed in accordance with techniques described in the above-referenced PCT Publication Nos. WO 99/03533 and WO 97/25098 and their corresponding U.S. National Phase application Ser. Nos. 09/481,253, which issued as U.S. Pat. Nos. 6,571,127, and 09/101,723, which issued as U.S. Pat. No. 6,317,631, mutatis mutandis.

Typically, evaluation apparatus 18 includes remote operator controls 71, external to the patient's body. This remote unit is typically configured to enable the patient or his physician to change parameters of the ingestion schedule stored in memory block 88. For example, if the patient has lost weight, the physician may change the ingestion schedule to allow a single mid-afternoon snack. Alternatively or additionally, operator controls 71 comprise an override button, so that the patient may eat outside of the designated meal times, or consume a particular food or drink not in accordance with the schedule, if the need arises. Operator controls 71 typically communicate with control unit 90 using standard methods known in the art, such as magnetic induction or radio frequency signals.

FIG. 4 is a schematic diagram showing experimental apparatus 60 used to measure electrical responses to eating in the stomach 64 of a normal rabbit, in accordance with a typical embodiment of the present invention. Bipolar sense electrodes 62 were coupled to the fundus of stomach 64, and bipolar sense electrodes 63 were coupled to the antrum of the stomach. Additionally, two stitch electrodes 66 with a strain gauge 68 located therebetween were coupled to the antrum.

Figure 5:
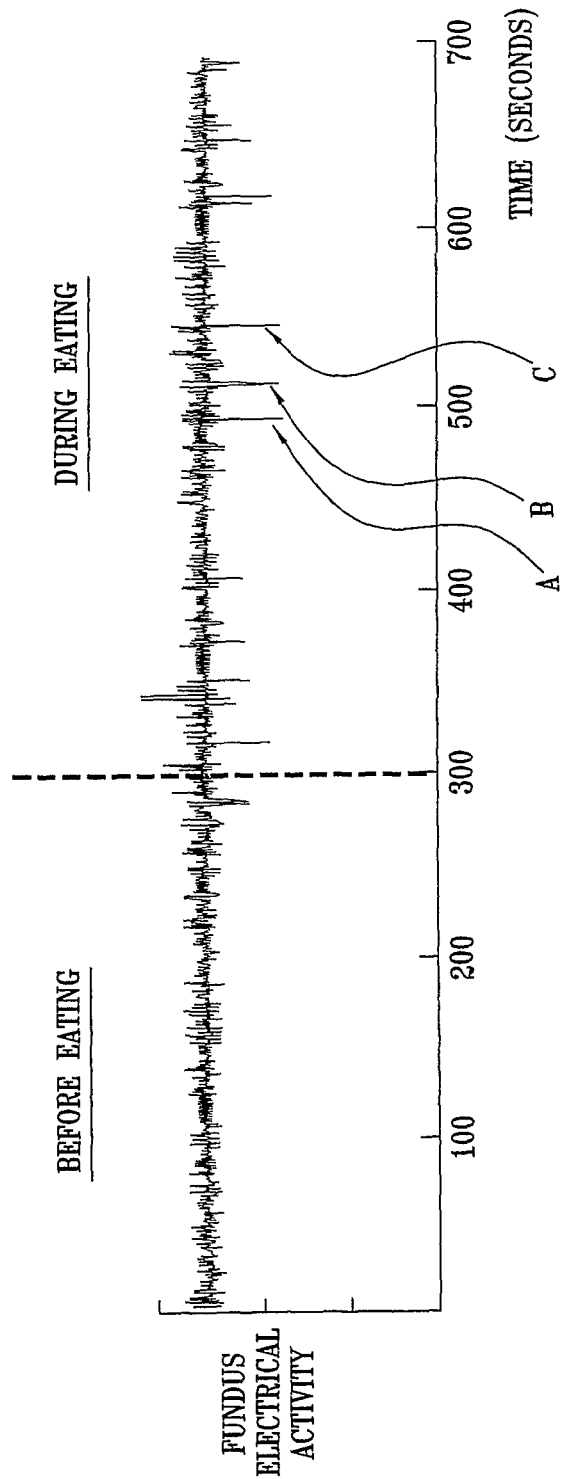
FIG. 5 is a graph showing electrical activity in the fundus of a normal rabbit before and during eating, and results of analysis thereof, in accordance with a typical embodiment of the present invention.

Reference is now made to FIGS. 5, 6A and 6B, which are graphs showing the results of experiments performed using apparatus 60 in a rabbit, in accordance with a typical embodiment of the present invention. FIG. 5 shows electrical activity in the fundus, measured during a five minute period before the rabbit was fed solid food, and during a more than six minute period while the rabbit was eating solid food. It can be seen that the second period is distinguished by markedly increased electrical activity. Spikes, typified by those marked "A," "B," and "C" in this graph, are typically identified by a control unit operating in accordance with these embodiments of the present invention, and are interpreted as indications of eating. It is noted that in the case of the rabbit experiment shown in FIG. 5, electrical activity as measured by spikes per unit time increased by a factor of about 8, and is therefore considered to be a good indication of the initiation and continuation of eating.

FIG. 6A is a graph showing the electrical response of the fundus of the rabbit stomach, and the results of analysis thereof, in accordance with an embodiment of the present invention. In this experiment, the measurements were first taken for five minutes while the rabbit was eating solid food, and were continued for almost 10 minutes after the rabbit ceased eating. It is clearly seen that the period after the rabbit ate is characterized by significantly less electrical activity than that which occurred during eating. Spikes, such as those marked "A," "B," and "C" in this graph, occur at a rate at least 15 times higher during eating than thereafter, and are therefore typically used by a control unit to determine both the onset and the termination of eating.

FIG. 6B is an expanded view of some of the data shown in FIG. 6A, additionally showing simultaneous mechanical and electrical activity in the antrum of the rabbit. The top graph shows mechanical activity in the antrum as measured by strain gauge 68 (FIG. 4), and the middle graph shows electrical activity in the antrum, measured by electrodes 63 during the same time period. The repeated co-occurrence of antral mechanical and electrical activity, as seen in FIG. 6B, is indicative of the expected antral mechanical response to antral electrical activity.

The bottom graph of FIG. 6B shows the measured electrical activity in the fundus during the same period, i.e., while the rabbit was eating. It can be seen that, while there is close correlation between mechanical and electrical activity in the antrum, there is not such a close correlation between fundic electrical activity and either measure of antral activity. Control unit 90 (FIG. 2) is therefore generally enabled to measure and differentiate between fundic and antral response, and to utilize this information to facilitate the evaluations and determinations described herein.

Figure 7:
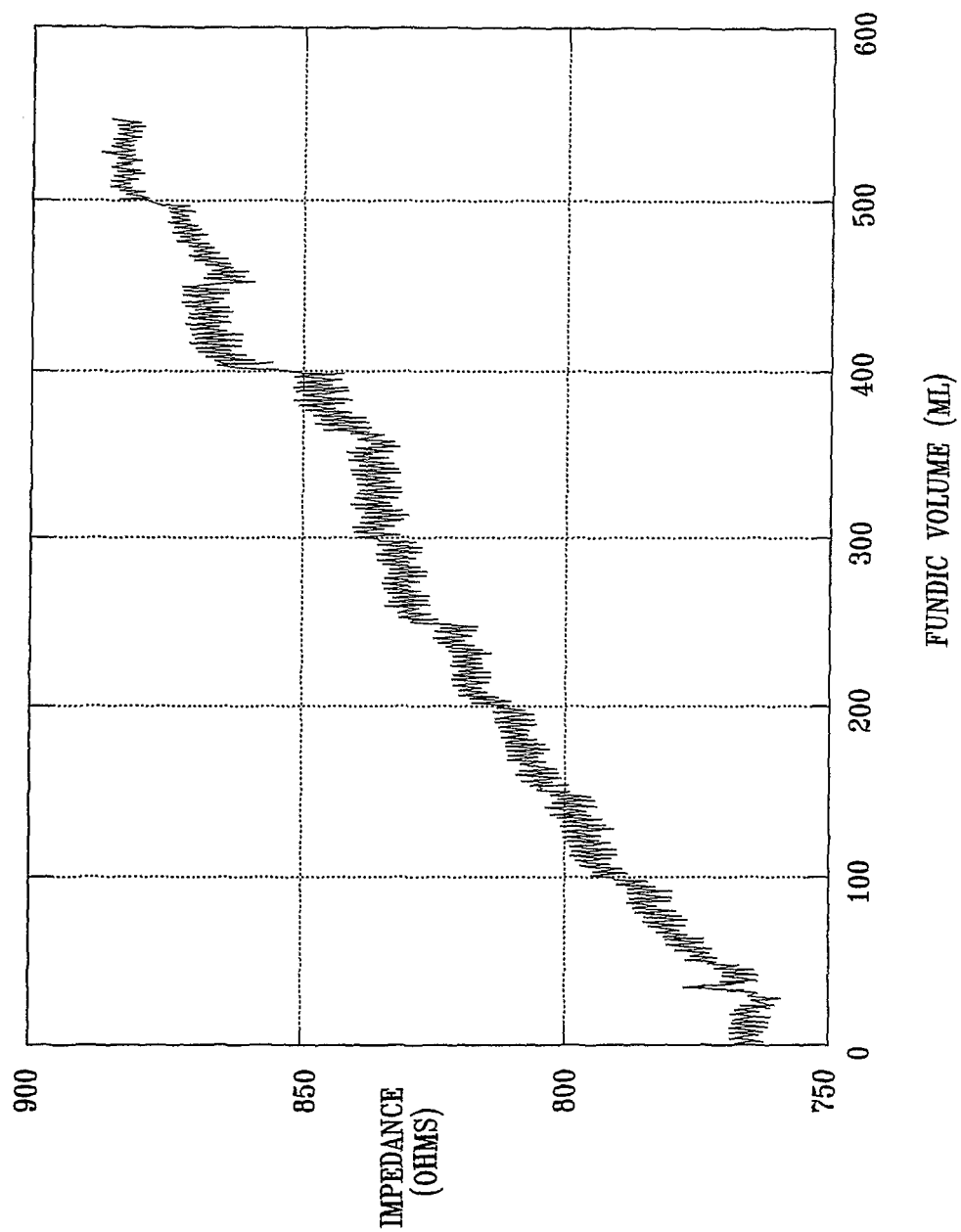
FIG. 7 is a graph showing detail of electrical fundic activity, measured in accordance with a typical embodiment of the present invention.

FIG. 7 is a graph showing electrical impedance measurements made between two stitch electrodes placed in the stomach of a pig, in accordance with an embodiment of the present invention. In this experiment, fundic volume was measured at the same time as the impedance was measured, and the data show a clear dependence of the impedance on the volume. It is hypothesized that as the fundus distends, the fundic wall thickness decreases, producing a corresponding increase in electrical impedance. Alternatively or additionally, the increased distance between the two electrodes produced as a result of the distension causes the electrical impedance to increase. Similar experimental results (not shown) were obtained when impedance and volume measurements were made in the antrum. Moreover, changes in impedance were found to correlate with waves of antral activity.

Reference is now made to FIGS. 8, 9, 10, and 1, which are graphs showing the results of experiments performed using apparatus (not shown) similar to apparatus 60 in several normal dogs, in accordance with a typical embodiment of the present invention. All of the dogs fasted for approximately 24 hours prior to eating during the experiments.

Figure 8:
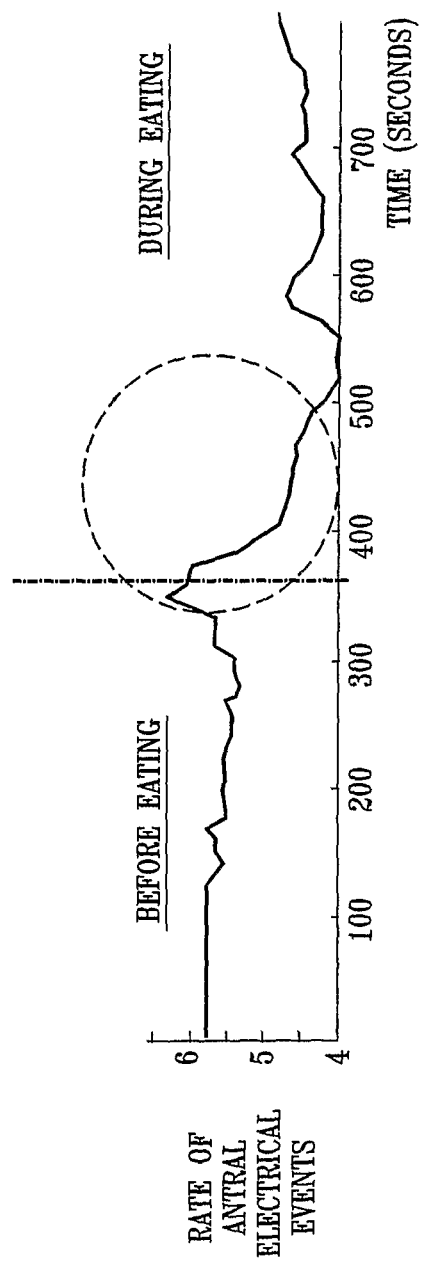
FIG. 8 is a graph showing the rate of electrical events in the antrum of a normal dog before and during eating, and results of analysis thereof, in accordance with a typical embodiment of the present invention.

FIG. 8 shows the rate of electrical events in the antrum in a dog, measured during a six minute period before the dog was fed solid food and during a more than seven minute period while the dog was eating solid food. Electrical events that were recorded were spikes in the signal of amplitude at least a threshold amount greater than the signal noise. It will be appreciated that detecting changes in other events may be useful for some applications. It will also be appreciated that whereas data shown in the figures reflects measurements of antral electrical events, for some applications the analysis techniques described herein may also be implemented with respect to the rate of fundic electrical events.

It can be seen that the second period is distinguished by a markedly decreased rate of antral electrical events. Such a decrease is typically identified by a control unit operating in accordance with these embodiments of the present invention, and is interpreted as an indication of eating. It is noted that the rate of antral electrical events, as measured by events per unit time, decreased on average by about 20% beginning about one minute after the initiation of eating, and is therefore considered to be a good indication of the initiation and continuation of eating. (Decreases of up to about 50% were seen in other experiments.) Alternatively or additionally, responsive to a calibration procedure, such a decrease in the rate of antral electrical events may be used to determine other characteristics of the ingested material, for example, its nutritional, chemical, and/or caloric content. Similar results were obtained in experiments on two other dogs (not shown).

FIG. 9 is a graph showing the rate of electrical events in the antrum in a second dog, measured during a more than 40 minute period before the dog was fed solid food, during an approximately 13 minute period while the dog was eating solid food (interrupted by an approximately 6 minute period of non-eating), and during an almost 60 minute period after the dog ceased eating. It is clearly seen that the period beginning approximately four minutes after the dog ceased eating is characterized by return to a rate of antral electrical events almost equal to the rate prior to eating, and significantly higher than the reduced rate during eating. The rate of antral electrical events is therefore typically used by a control unit to determine both the onset and the termination of antral activity.

FIG. 10 is a graph showing simultaneous mechanical activity, electrical activity, and rate of electrical events in the antrum of a third dog, measured during a more than 16 minute period before the dog was fed solid food, during an approximately 3.5 minute period while the dog was eating solid food, and during a more than four minute period after the dog ceased eating. The top graph shows mechanical activity in the antrum as measured by a strain gauge, and the middle graph shows electrical activity in the antrum, measured by electrodes during the same time period. It can be seen that co-occurring mechanical and electrical activity began approximately 1.5 minutes prior to the beginning of eating, corresponding with the onset of cephalic phase activity (brain activity reflecting the mental anticipation of eating).

The bottom graph of FIG. 10 shows the rate of electrical events in the antrum of the dog. It can be seen that the second period is distinguished by a markedly decreased rate of antral electrical events, consistent with the results of the first dog experiment described hereinabove. An increase in mechanical and/or electrical antral activity prior to eating as occurred in this experiment is typically identified by a control unit operating in accordance with these embodiments of the present invention, and provides additional information that can be interpreted together with information such as the decreased rate of antral electrical events observed in this experiment to provide indications of anticipation of eating, eating and/or gastric digestion.

FIG. 11 is a graph showing electrical impedance measurements made between two stitch electrodes in the fundus of a fourth dog, measured during five sequential periods: (1) an approximately 22 minute period before the dog was fed solid food (portion of period not shown), (2) an approximately three minute period while the dog was eating solid food, (3) an approximately 7.5 minute period during which the dog did not eat, (4) an approximately one minute period while the dog was eating solid food, and (5) a greater than 10 minute period after the dog ceased eating.

It can be seen that the eating periods (second and fourth periods) are distinguished by markedly increased fundic electrical impedance. Such increases are typically identified by a control unit operating in accordance with these embodiments of the present invention, and are interpreted as indications of eating. This interpretation is supported by the correlation between impedance and volume measurements in the fundus obtained in the pig experiments described hereinabove. It is noted that in the case of the dog experiment shown in FIG. 11, the fundic electrical impedance, as measured in ohms, increased by more than about 12%, beginning less than about one minute after the initiation of eating during the second period, and by about 5% beginning less than about one minute after the initiation of eating during the fourth period. The fundic electrical impedance is therefore considered to be a good indication of the initiation and continuation of eating. Similar results were obtained in two other experiments on different days on the same dog (not shown).

It is clearly seen in FIG. 11 that the period beginning almost immediately after the dog ceased eating (the fifth period) is characterized by a return of fundic electrical impedance to a value almost equal to that prior to eating, and significantly lower than the increased value observed during eating. Fundic electrical impedance is therefore typically used by a control unit to determine both the onset and the termination of eating.

The inventors have observed that fundic electrical impedance (e.g., as measured in the case of the dog experiment shown in FIG. 11), as an indicator of eating, typically exhibits lower variability than antral electrical impedance, and is less affected by movement and/or change in posture of the subject. Fundic electrical impedance also typically provides more reliable detection of eating than antral activity.

In typical embodiments of the present invention, measurements of antral and/or fundic electrical impedance are used in conjunction with or separately from other indicators of swallowing or digestion, described hereinabove, in order to track a patient's eating habits.

It will be recognized by persons skilled in the art that more complex combinations of variations in levels of electrical or mechanical activity in different regions of the stomach may occur than those demonstrated in the experiments described hereinabove. For example, certain electrical or mechanical activity may lag the eating of certain amounts and types of food. Examples of more complex combinations (not shown) were obtained in additional experiments in other dogs. Analysis block 80, with proper calibration as described hereinabove, can readily be enabled to evaluate such complex combinations.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Gastric apparatus, comprising:
   one or more sensors, configured to generate respective sensor signals responsive to activity of a gastrointestinal tract of a subject; and
   a control unit, configured with an eating detection threshold selected from the group consisting of: a predetermined threshold, and a threshold determined during a calibration procedure, and configured to:
   receive and analyze the sensor signals,
   identify an aspect of at least one of the sensor signals representing periodic activity of the gastrointestinal tract,
   modify the eating detection threshold responsive to identifying the aspect of the signals representing the periodic activity, and
   determine whether an eating event has occurred responsive to the modified eating detection threshold and at least one of the analyzed sensor signals,
   wherein the control unit is configured to modify the eating detection threshold responsive to identifying that the periodic activity is of a migrating motor complex (MMC).

2. The apparatus according to claim 1, wherein the control unit is configured to receive and analyze the sensor signals at a first time and a second time after the first time, and to modify the eating detection threshold responsive to a relationship between the sensor signals received at the first and the second times.

3. The apparatus according to claim 1, wherein the control unit is configured to identify the aspect representing the periodic activity which has a period of between 30 and 50 minutes.

4. The apparatus according to claim 1, wherein the one or more sensors comprise one or more implantable mechanical sensors.

5. The apparatus according to claim 1, wherein the one or more sensors comprise one or more implantable electrodes.

6. The apparatus according to claim 1, wherein the control unit is configured to identify the aspect representing the periodic activity which has a period of between 50 and 90 minutes.

7. The apparatus according to claim 1, wherein the control unit is configured to identify the aspect representing the periodic activity which has a period of between 90 and 120 minutes.

8. The apparatus according to claim 1, further comprising a set of one or more current-application electrodes, wherein the control unit is configured to drive the current-application electrodes to apply a current to tissue of the subject.

9. The apparatus according to claim 8, wherein the control unit is configured to drive the current-application electrodes to apply the current to the tissue in response to analysis of the eating event.

10. The apparatus according to claim 9, wherein the control unit is configured to drive the current-application electrodes to apply an ingestion control signal to the tissue in response to the analysis of the eating event.

11. The apparatus according to claim 10, wherein the control unit is configured to configure the ingestion-control signal to cause an effect in the subject selected from the group consisting of: a sensation of discomfort, a sensation of minor nausea, vertigo, pain, a contraction of the esophagus, a contraction of the lower esophageal sphincter, a feeling of satiation, and gastric dysrhythmia.

12. The apparatus according to claim 1, wherein the sensors are configured to be coupled to a stomach of the subject.

13. The apparatus according to claim 1, wherein the apparatus is configured to treat a condition of the subject.

14. The apparatus according to claim 13, wherein the apparatus is configured to treat obesity of the subject.

15. The apparatus according to claim 1, wherein the control unit is configured to apply a treatment to the subject in response to analysis of the eating event.

16. The apparatus according to claim 1, wherein the one or more sensors comprise at least two impedance sensors, which are configured to measure an electrical impedance between respective stomach sites, and wherein the eating detection threshold is an eating detection impedance threshold.

17. The apparatus according to claim 16, wherein the at least two impedance sensors are configured to measure the impedance between respective fundic sites, and wherein the eating detection impedance threshold is an eating detection fundic impedance threshold.

18. The apparatus according to claim 1, wherein the one or more sensors comprise at least one antral sensor, and wherein the control unit is configured to identify the aspect representing antral periodic electrical activity.

19. The apparatus according to claim 1, wherein the control unit is configured to determine that the eating event has occurred responsive to finding that a value of the at least one of the analyzed sensors signals crosses the modified eating detection threshold.

20. The apparatus according to claim 1, wherein the control unit is configured to determine a period of the periodic activity during a calibration period.

21. Gastric apparatus, comprising:
   one or more sensors, configured to generate respective sensor signals responsive to activity of a gastrointestinal tract of a subject; and
   a control unit, configured with an eating detection threshold selected from the group consisting of: a predetermined threshold, and a threshold determined during a calibration procedure, and configured to:
   receive and analyze the sensor signals,
   identify an aspect of at least one of the sensor signals representing periodic activity of the gastrointestinal tract, modify the eating detection threshold responsive to identifying the aspect of the signals representing the periodic activity, and determine whether an eating event has occurred responsive to the modified eating detection threshold and at least one of the analyzed sensor signals, wherein in modifying the eating detection threshold, the control unit is configured to modify the eating detection threshold in a threshold-modification direction, and wherein the control unit is configured, at a later time at least 30 minutes following modifying the eating detection threshold, to further modify the eating detection threshold in the threshold-modification direction responsive to identifying at the later time the aspect of the signals representing the periodic activity.

22. Gastric apparatus, comprising:

one or more sensors, configured to generate respective sensor signals responsive to activity of a gastrointestinal tract of a subject; and a control unit, configured with an eating detection threshold selected from the group consisting of: a predetermined threshold, and a threshold determined during a calibration procedure, and configured to:

receive and analyze the sensor signals, identify an aspect of at least one of the sensor signals representing periodic activity of the gastrointestinal tract, modify the eating detection threshold responsive to identifying the aspect of the signals representing the periodic activity, and determine whether an eating event has occurred responsive to the modified eating detection threshold and at least one of the analyzed sensor signals, wherein the control unit is configured, at a later time at least 30 minutes following modifying the eating detection threshold, to at least partially restore the eating detection threshold towards a previous value thereof, responsive to not identifying at the later time the aspect of the signals representing the periodic activity.

23. The apparatus according to claim 22, wherein the control unit is configured to modify the eating detection threshold responsive to identifying that the periodic activity is of a migrating motor complex (MMC).

24. Gastric apparatus, comprising:

one or more sensors, configured to generate respective sensor signals responsive to activity of a gastrointestinal tract of a subject; and a control unit, configured with an eating detection threshold selected from the group consisting of: a predetermined threshold, and a threshold determined during a calibration procedure, and configured to:

receive and analyze the sensor signals, identify an aspect of at least one of the sensor signals representing periodic activity of the gastrointestinal tract, modify the eating detection threshold responsive to identifying the aspect of the signals representing the periodic activity, and determine whether an eating event has occurred responsive to the modified eating detection threshold and at least one of the analyzed sensor signals, wherein the control unit is configured to receive and analyze the sensor signals at a first time and a second time after the first time, and to modify the eating detection threshold responsive to a relationship between the sensor signals received at the first and the second times, and wherein the control unit is configured to modify the eating detection threshold responsive to the relationship, wherein the first time is between 30 and 50 minutes prior to the second time.

25. The apparatus according to claim 24, wherein the control unit is configured to identify the sensor signals received at the first time as representing a migrating motor complex (MMC) and to identify the sensor signals received at the second time as representing a MMC, and to modify the eating detection threshold responsive to identifying the sensor signals received at the first and the second times as representing the MMC.

* * * * *

UNITED STATES PATENT AND TRADEMARK OFFICE
CERTIFICATE OF CORRECTION

PATENT NO.        : 8,612,016 B2  
APPLICATION NO. : 11/573722  
DATED             : December 17, 2013  
INVENTOR(S)       : Kliger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this
Twenty-second Day of September, 2015

Michelle K. Lee
*Director of the United States Patent and Trademark Office*